(12) United States Patent
Limaye et al.

(10) Patent No.: US 11,904,150 B2
(45) Date of Patent: Feb. 20, 2024

(54) HYPODERMIC SAFETY NEEDLE

(71) Applicant: Becton, Dickinson and Company, Franklin Lakes, NJ (US)

(72) Inventors: Amit Uday Limaye, Wayne, NJ (US); David Poganski, Airmont, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 187 days.

(21) Appl. No.: 17/315,867

(22) Filed: May 10, 2021

(65) Prior Publication Data
US 2021/0353872 A1 Nov. 18, 2021

Related U.S. Application Data

(60) Provisional application No. 63/077,041, filed on Sep. 11, 2020, provisional application No. 63/023,481, filed on May 12, 2020.

(51) Int. Cl.
*A61M 5/32* (2006.01)
*A61M 5/34* (2006.01)
*A61M 5/50* (2006.01)

(52) U.S. Cl.
CPC ........ *A61M 5/3202* (2013.01); *A61M 5/3213* (2013.01); *A61M 5/3216* (2013.01);
(Continued)

(58) Field of Classification Search
CPC .... A61M 5/24; A61M 5/3202; A61M 5/3213; A61M 5/3216; A61M 5/3245;
(Continued)

(56) References Cited

U.S. PATENT DOCUMENTS 2,929,510 A 3/1960 Penn
3,101,841 A 8/1963 Baldwin
(Continued)

FOREIGN PATENT DOCUMENTS

EP 0200393 A1 11/1986
EP 0820778 A1 1/1998
(Continued)

OTHER PUBLICATIONS

PCT International Search Report and Written Opinion in PCT/US2020/031769 dated Aug. 12, 2021, 12 pages.
(Continued)

*Primary Examiner* — Tasnim Mehjabin Ahmed
(74) *Attorney, Agent, or Firm* — Servilla Whitney LLC

(57) ABSTRACT

A safety needle device for connection to a medical connector, including threaded connections. The safety needle comprises a collar configured to interdigitate with a conventional needle hub, the collar having attachment points for a hinged cap, the hinged cap being in a two-piece configuration. In further embodiments, the safety needle device comprises a removable hard needle cover configured to cover needle cannula and a distal portion of a needle hub. The hard needle enclosure further comprises a cap configured to interdigitate with the needle cover and cover a proximal portion of the needle hub. The cap and at least a portion of the needle cover are covered by a removable sleeve which holds the cap and the needle cover together. Even further embodiments comprise a needle hub, a needle cover, an adapter and a cap, the adapter configured to attach to a conventional needle cap.

24 Claims, 18 Drawing Sheets

(52) U.S. Cl.
CPC ............ *A61M 5/3245* (2013.01); *A61M 5/34* (2013.01); *A61M 5/345* (2013.01); *A61M 5/346* (2013.01); *A61M 5/348* (2013.01); *A61M 5/5086* (2013.01); *A61M 2205/6063* (2013.01)

(58) Field of Classification Search
CPC ........ A61M 5/34; A61M 5/345; A61M 5/346; A61M 5/348; A61M 5/5086; A61M 5/002; A61M 5/321; A61M 5/3293; A61M 2205/6063; A61M 2005/3109
See application file for complete search history.

(56) References Cited

U.S. PATENT DOCUMENTS

| | | | |
|---|---|---|---|
| 3,149,717 A | | 9/1964 | Castelli |
| 3,245,567 A | | 4/1966 | Knight |
| 4,820,277 A | * | 4/1989 | Norelli ................ A61M 5/3216 604/263 |
| 4,950,249 A | * | 8/1990 | Jagger ................ A61M 5/3216 604/263 |
| 5,591,134 A | * | 1/1997 | Shu ..................... A61M 5/3216 604/263 |
| 5,733,265 A | * | 3/1998 | Bachman ............ A61M 5/3216 604/263 |
| 6,413,243 B1 | * | 7/2002 | Geist ................... A61M 5/3216 604/110 |
| 2003/0078548 A1 | * | 4/2003 | Kobayashi .......... A61M 5/3216 604/263 |
| 2008/0033362 A1 | * | 2/2008 | Hwang ............... A61M 5/3216 604/164.08 |
| 2008/0108951 A1 | | 5/2008 | Jerde et al. |
| 2021/0361882 A1 | * | 11/2021 | Jacquemet .......... A61M 5/3221 |

FOREIGN PATENT DOCUMENTS

| | | |
|---|---|---|
| EP | 1093784 A2 | 4/2001 |
| EP | 1208860 A1 | 5/2002 |
| EP | 1312389 A1 | 5/2003 |
| EP | 2455127 B1 | 5/2012 |
| GB | 1191634 A | 5/1970 |
| WO | 91/09639 A2 | 7/1991 |
| WO | 2004110535 A1 | 12/2004 |
| WO | 2019149655 A1 | 8/2019 |

OTHER PUBLICATIONS

PCT International Search Report and Written Opinion in PCT/US2021/031768 dated Aug. 11, 2021, 13 pages.

PCT International Search Report and Written Opinion in PCT/US2021/031771 dated Aug. 6, 2021, 13 pages.

\* cited by examiner

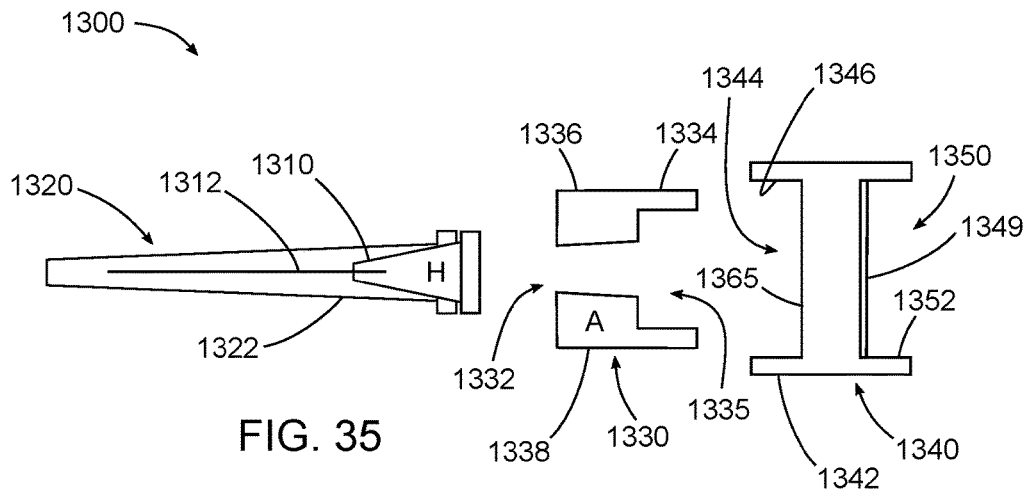
FIG. 35
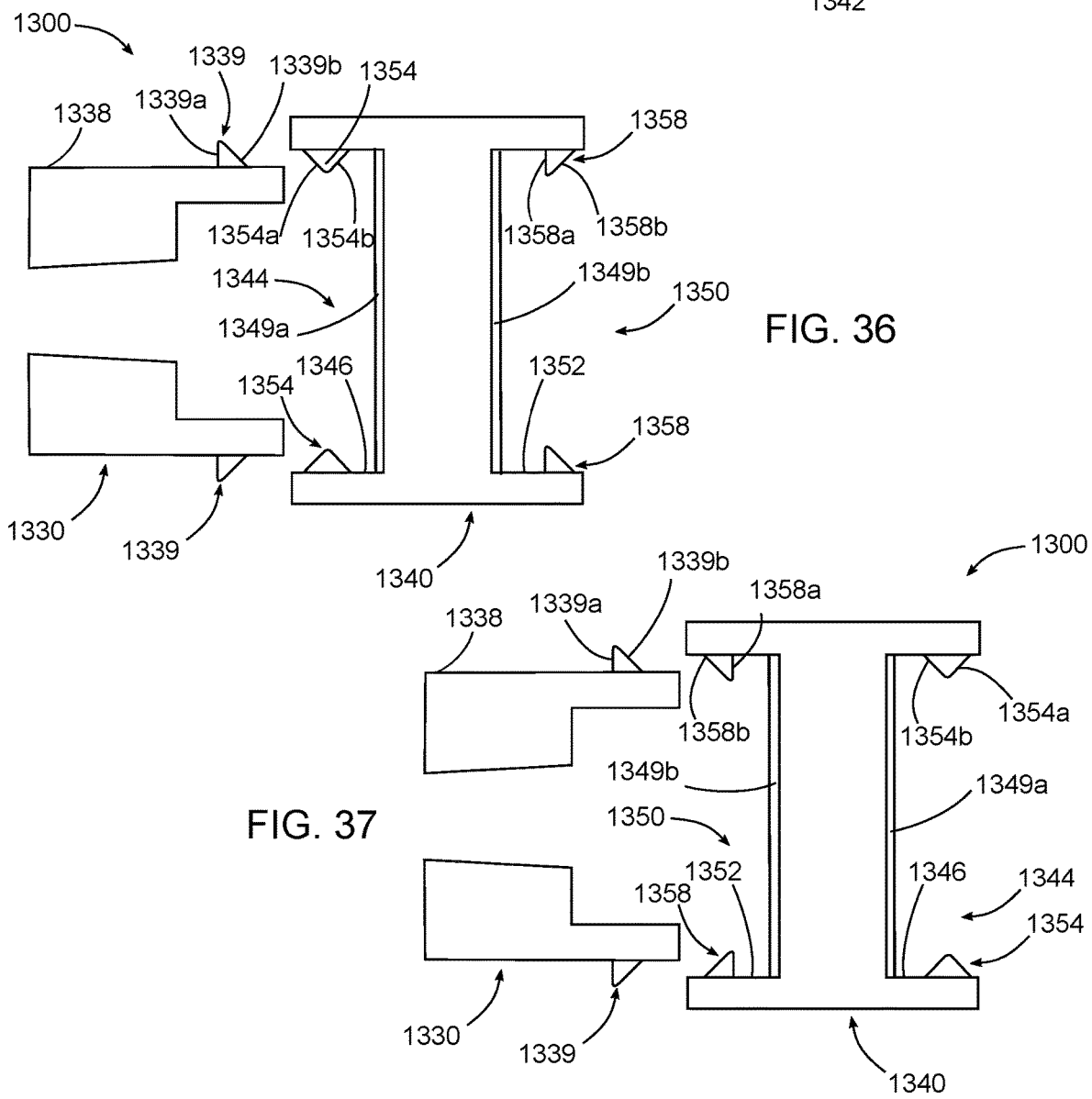
FIG. 36
FIG. 37

HYPODERMIC SAFETY NEEDLE

CROSS-REFERENCE TO RELATED APPLICATIONS

This application claims priority under 35 U.S.C. § 119(e) to U.S. Provisional Application No. 63/023,481, filed May 12, 2020, and U.S. Provisional Application No. 63/077,041, filed Sep. 11, 2020, the disclosures of which are incorporated herein by reference in their entirety.

TECHNICAL FIELD

The present disclosure relates to a hypodermic safety needle having a simplified design for reducing raw materials and faster molding and production processes. The present disclosure generally relates to a passive safety needle device which combines the packaging and safety aspects into a single design.

BACKGROUND

Clean or sterile articles particularly useful for medical applications are packaged to preserve their sterility. The packaging for these articles is intended to provide a barrier to prevent microorganisms from entering inside the packaging to contaminate its contents. In most instances, the packaging is opened immediately prior to using the article, such as with a blister pack housing a needle, so as to minimize the time period in which the article is exposed to unsterile conditions. After use of the needle, package is discarded separate from the needle.

Needle devices are used throughout the medical industry for the injection and withdrawal of a wide variety of fluids and solutions into and from the human body. Because of the numerous potential hazards associated with the handling and manipulation of bodily fluids, and particularly blood, there are a number of known safety features that are frequently incorporated into various types of needle devices to protect the practitioner from accidental exposure to the needle.

The "conventional" hypodermic needle is retrieved from a blister package, the needle shield is removed and then the plastic hub is attached to a luer lock or luer slip syringe. Drug from a vial is then retrieved and administered to the patient via injection. The needle is then discarded either as is or after capping using a recommended method of capping. On the other hand, a safety needle has an extra step wherein an additional component, the safety shield, is deployed to permanently "engulf" the needle thereby making it inaccessible. This ensures that the needle cannot be reused and also contributes to healthcare worker safety—by protecting them from contaminated needle stick injury.

This extra step is enabled by either a unique hub design that acts as a base for the safety mechanism to attach onto or a very complicated safety shield mechanism. This hub is bulkier and more difficult to mold compared to a conventional needle hub. Similarly the safety mechanism itself is also composed of a component that is difficult to mold and is also bulky. The needle shield is made of a thick walled plastic to ensure the needle does not get damaged pre-use. Additionally the needle shield that protects the needle pre-use finds no utility post use and is discarded adding to the plastic usage.

Such features are limited in their purpose. The needle shield merely protects during transportation and storage, playing no role in safety features of the device. The safety shield is an intricately molded part and interfaces with a needle hub, the connection of the safety shield to the needle hub also being intricately molded, resulting in higher cost for the two components. Thus, there is a need to provide a safety needle device incorporating both features of needle shields and safety shields while reducing manufacturing costs, including materials and molding complexity. Furthermore, there is a need to provide a hard needle enclosure or hard needle cover that provides needle sterility and eliminates the need for a blister pack.

SUMMARY

A first aspect of the present disclosure relates to a safety needle device comprising a needle hub, a needle cannula, a removable collar and a two-piece hinged cap having two elongated bodies in a clamshell configuration. The needle hub is configured to couple to a syringe comprising a distal portion and a proximal portion, the needle hub having a substantially cylindrical shape. The needle cannula extends from the distal portion of the needle hub. The removable collar has a substantially cylindrical body, an aperture extending through the substantially cylindrical body, and two attachment points disposed on an outer surface of the collar, the aperture being sized and configured to receive the proximal portion of the needle hub; the two attachment points being configured to attach to a two-piece hinged cap. The two-piece hinged cap has two elongated bodies in a clamshell configuration, the two elongated bodies configured to close in on one another, each of the elongated bodies having a semicircular cross-section and a cavity defined by an open proximal end and a closed distal end, loops extend from the open proximal end, the loops configured to interdigitate with the two attachment points of the collar.

In one or more embodiments of the first aspect, the proximal portion of the needle hub tapers in a distal direction. In one or more embodiments, the needle hub further comprises an at least one thread included on an outer surface of the proximal portion of the needle hub, the at least one thread configured to engage with a standard ISO-2 type of luer fitting. In one or more embodiments of the first aspect, the aperture of the collar is sized and configured to create an interference fit with the proximal portion of the needle hub.

In one or more embodiments of the first aspect, the aperture of the collar is sized and configured to create a loose fit with the proximal portion of the needle hub. In one or more embodiments, the collar freely rotates around the proximal portion of the needle hub. In one or more embodiments, the collar is configured to snap into the needle hub creating an interference fit, the collar being configured to freely rotate only upon application of sufficient force, thereby resisting free movement. In one or more embodiments, the two attachment points are configured as hooks sized to receive loops of the two-piece hinged cap. In one or more embodiments of the first aspect, the two attachment points are sized and shaped to create a snap fit with the loops of the two-piece hinged cap.

In one or more embodiments of the first aspect, the two attachment points create an interference fit with the loops configured to resisting free movement. In one or more embodiments of the first aspect, the collar and two piece hinged cap are integrally formed. In one or more embodiments, the two attachment points are configured as a living hinge. In one or more embodiments of the first aspect, the living hinge is configured to have a residual spring action, wherein the living hinge is in an open state in its resting position. In one or more embodiments of the first aspect, the open state of the living hinge resists movement of the two-piece hinged cap. In one or more embodiments of the first aspect, the elongated bodies of the two-piece hinged cap are configured to snap together upon full closure. In one or more embodiments of the first aspect, two-piece hinged cap is configured to freely move and the collar is configured to freely rotate around the needle hub in an open state of the safety needle device.

In one or more embodiments of the first aspect, the two-piece hinged cap is configured to rotate whereby the practitioner has a clear view of markings disposed on the barrel of the syringe to ensure that a correct dosage is metered. In one or more embodiments of the first aspect, the two-piece hinged cap is configured to move away from a barrel of a syringe whereby the practitioner has a clear view of markings disposed on the barrel of the syringe to ensure that a correct dosage is metered.

In one or more embodiments of the first aspect, each of the two-piece hinged cap is freely able to open or close independently. In one or more embodiments of the first aspect, one of the two-piece hinged cap is movable independent from the other of the one of the two-piece hinged cap. In one or more embodiments, the needle cannula is fully exposed in the open state. In one or more embodiments, the two-piece hinged cap is movable from 0 degrees with respect to the cannula to at least degrees with respect to the needle cannula. In one or more embodiments of the first aspect, the two-piece hinged cap is closed on itself in a closed state. In one or more embodiments, the safety needle device is packaged and supplied in the closed state. In one or more embodiments of the first aspect, the two-piece hinged cap is held closed by a disposable plastic seal or sleeve disposed over the two-piece hinged cap.

In one or more embodiments of the first aspect, the closed distal end of the two-piece hinged cap is configured to non-removably lock upon closure of the two-piece hinged cap. In one or more embodiments, the safety needle device further comprises a sleeve disposed over the two-piece hinged cap in a closed state, the sleeve movable in a longitudinal direction over the two piece hinged cap. In one or more embodiments, the closed distal end of the two-piece hinged cap is configured to non-removably lock upon closure of the two-piece hinged cap, the closed distal ends defining a final closed state. In one or more embodiments of the first aspect, the two-piece hinged cap further comprises a locking mechanism disposed a distance from a closed distal end of the two-piece hinged cap.

In one or more embodiments of the first aspect, the locking mechanism comprises a hook tab projecting from an edge of one of the two-piece hinged cap and a corresponding aperture disposed within the cavity of the other of the two-piece hinged cap. In one or more embodiments of the first aspect, the aperture is configured to interdigitate and removably or non-removably receive the hook tab.

In one or more embodiments of the first aspect, the aperture is configured to interdigitate and removably receive the hook tab in a closed state. In one or more embodiments of the first aspect, the aperture is configured to interdigitate and non-removably receive the hook tab in a closed state. In one or more embodiments, the locking mechanism comprises an aperture disposed within a cavity of the of one of the two-piece hinged cap and a corresponding hook tab projecting from an edge of the other of the two-piece hinged cap. In one or more embodiments of the first aspect, the safety needle device further comprising push features disposed on the elongated bodies of the two-piece hinged cap.

In one or more embodiments of the first aspect, the push features has a triangular shape, the triangular shape having a hypotenuse face configured to abut a barrel surface of a syringe when the needle hub is connected to the luer connector of the syringe. In one or more embodiments, the hypotenuse face is configured to aid in pushing the two-piece hinged cap together. In one or more embodiments of the first aspect, a right face of the triangular shape is configured to aid in pulling the two-piece hinged cap apart.

In one or more embodiments of the first aspect, an aperture extending through a right face of the triangular shape forms an edge between the aperture and the hypotenuse face, the hypotenuse face configured to aid in pulling the two-piece hinged cap apart. In one or more embodiments of the first aspect, the push features are configured as tabs protruding from the elongated bodies of the two-piece hinged cap. In one or more embodiments of the first aspect, the tabs comprise a neck, a thumb press surface and a barrel engaging surface, the barrel engaging surface configured to abut the barrel surface of the syringe when a needle hub is connected to a luer connector of the syringe. In one or more embodiments, the thumb press surface is configured to aid in pushing the two-piece hinged cap onto one another. In one or more embodiments of the first aspect, a distal edge of the thumb press surface is configured to allow the practitioner to pull the two-piece hinged cap apart.

In one or more embodiments of the first aspect, the thumb press surface is substantially parallel to the two-piece hinged cap. In one or more embodiments of the first aspect, the barrel engaging surface extends at an angle to the thumb press surface. In one or more embodiments of the first aspect, the barrel engaging surface extends at a right angle to the thumb press surface. In one or more embodiments, the thumb press surface is disposed on the neck, the thumb press surface being at a substantially right angle to the two-piece hinged cap, the barrel engaging surface extending at a right angle from the thumb press surface.

A second aspect of the present disclosure relates to a hard-packaged safety needle device comprising a needle hub, a needle cannula and a hard needle enclosure including a needle cover and a cap. The needle hub is configured to couple to a syringe comprising a distal portion and a proximal portion, the needle hub having a substantially cylindrical shape. The needle cannula extends from the distal portion of the needle hub. The needle cover has an elongated body, a cavity defined by an open proximal end and a closed distal end, a proximal portion, a medial portion and a distal portion, the proximal portion having a cylindrical surface configured to mate with a cap, the medial portion being defined by a flange extending from the elongated body, the elongated body further having an inner surface of the cavity having a proximal inner surface, a medial inner surface, and a distal inner surface, the proximal inner surface including a ribbed surface configured to create an interference fit with the proximal portion of the hub. The cap includes a substantially cylindrical body having an open distal end, a closed proximal end, and a cavity defined by the open distal end and the closed proximal end, the open distal end of the cap abutting the open proximal end of the needle cover.

In one or more embodiments of the second aspect, the needle hub further comprises a plurality of longitudinal ribs extending from the distal portion of the needle hub. In one or more embodiments, the medial inner surface of the needle cover includes a plurality of protrusions extending from the medial surface, the plurality of protrusions being configured to interdigitate with the plurality of longitudinal ribs of the needle hub. In one or more embodiments of the second aspect, each of the plurality of longitudinal ribs nest between two of the plurality of protrusions, preventing rotational movement of the needle hub. In one or more embodiments of the second aspect, a removable interference fit is created between the proximal portion of the needle hub and the ribbed surface of the proximal inner surface.

In one or more embodiments of the second aspect, the cap further comprises a plurality of protrusions extending from an inner surface of the cavity of the cap, the plurality of protrusions extend longitudinally from the inner surface. In one or more embodiments of the second aspect, the plurality of protrusions of the cap comprises a distal portion adjacent to the open distal end of the cap, the distal portion tapering inwardly from the open distal end the taper configured to create an interference fit with the proximal portion of the needle cover upon insertion of the cap over the proximal portion of the needle cover. In one or more embodiments of the second aspect, a proximal portion of the plurality of protrusions of the cap extends further from the inner surface of the cap and is configured to abut the proximal portion of the needle hub upon insertion of the cap over the proximal portion of the needle cover. In one or more embodiments, the hard needle enclosure further comprises a sleeve formed into a cylindrical shape comprising an open proximal end, an open distal end and a plurality of perforations disposed radially around the cylindrical shape, the plurality of perforations configured to break upon separation of the needle cover from the cap.

In one or more embodiments of the second aspect, the sleeve further comprising a tab integrally formed with the sleeve. In one or more embodiments of the second aspect, the tab includes labeling or instructions. In one or more embodiments, the sleeve is heat-sealed to the needle cover the cap. In one or more embodiments of the second aspect, the sleeve configured as a tamper-evident seal. In one or more embodiments of the second aspect, the sleeve fully covers the cap and the proximal end of the needle cover. In one or more embodiments, the plurality of perforations are near or directly over the open distal end of the cap and the open proximal end of the needle cover when the hard needle enclosure is assembled.

A third aspect of the present disclosure relates to a hard-packaged safety needle device comprising a needle hub, a needle cannula, and a hard enclosure including a needle cover, an adapter and a cap. The needle hub is configured to couple to a syringe comprising a distal portion and a proximal portion, the needle hub having a substantially cylindrical shape. The needle cannula extends from the distal portion of the needle hub. The needle cover is configured to house the needle cannula and the distal portion of the needle hub, the needle cover having a tapered cylindrical outer surface. The adapter has a substantially cylindrical body including a proximal portion, a distal portion and an outside cylindrical surface, the distal portion having a tapered aperture configured to create an interference fit and a sterility barrier with the tapered cylindrical outer surface of the needle cover, the proximal portion having a second cavity in communication with the tapered aperture. The cap has a substantially cylindrical shape including a distal opening defining a first cavity, the cap being configured to interdigitate with the adapter by the first cavity of the cap receiving the proximal portion of the adapter.

In one or more embodiments of the third aspect, the outside cylindrical surface creates or forms an interference fit and a sterility barrier with an inside surface of the first cavity when the adapter and the cap first cavity are connected. In one or more embodiments, the outside cylindrical surface creates or forms a snap fit and a sterility barrier with the inside surface of the first cavity when the adapter and the cap first cavity are connected. In one or more embodiments of the third aspect, the outside cylindrical surface is removably bonded with adhesive onto the inside surface of the first cavity. In one or more embodiments of the third aspect, the outside cylindrical surface is threaded into the inside surface of the first cavity.

In one or more embodiments of the third aspect, the tapered aperture of the adapter is configured to interdigitate with a conventional needles or a commercially available needle. In one or more embodiments, the hard needle enclosure further comprises a hinge having a distal connection to the outside cylindrical surface of the adapter and a proximal connection to an outside cylindrical surface of the cap. In one or more embodiments of the third aspect, the hard needle enclosure is opened with one handed operation by applying a proximal force F against the outside cylindrical surface of the adapter opposite the hinge. In one or more embodiments of the third aspect, the proximal opening and the distal opening are removably bonded together with adhesive.

In one or more embodiments of the third aspect, the hard needle enclosure further comprises a label disposed on a distal wall of the first cavity of the cap. In one or more embodiments of the third aspect, the label indicates that the hard needle enclosure has been opened or used. In one or more embodiments of the third aspect, the label includes words, numbers or symbols. In one or more embodiments, the label includes a biohazard symbol.

In one or more embodiments of the third aspect, the cap further comprises a second cavity having an inside surface, the second cavity of the cap being configured to interdigitate with the adapter. In one or more embodiments, the outside cylindrical surface of the adapter creates or forms an interference fit and a sterility barrier with an inside surface of the first cavity when the adapter and the cap first cavity are connected. In one or more embodiments of the third aspect, the adapter further comprises a ledge having a triangular shape, wherein a right face of the ledges is located opposite a sloped surface of the ledge, the ledge of the adapter disposed on the outside surface of the adapter.

In one or more embodiments of the third aspect, the cap comprises a holding tab disposed on the inside surface of the first cavity, the tab configured to removably snap-fit with the ledge of the adapter upon insertion of the adapter into the first cavity of the cap. In one or more embodiments of the third aspect, the cap further comprises a ledge including a locking surface disposed on the inside surface of the first cavity, the ledge of the cap having a triangular shape, wherein a right face of the ledge of the cap is located opposite a sloped surface of the ledge, the ledge of the cap being configured to create a non-removable snap fit with the ledge of the adapter upon insertion of the adapter into the second cavity of the adapter.

BRIEF DESCRIPTION OF THE DRAWINGS

FIG. 35 illustrates an exploded cross-sectional view of a hard needle enclosure according to a sixth embodiment of the present disclosure;

FIG. 36 illustrates an exploded cross-sectional view of the hard needle enclosure according to the sixth embodiment of the present disclosure; and FIG. 37 illustrates an exploded cross-sectional view of the hard needle enclosure according to the sixth embodiment of the present disclosure.

DETAILED DESCRIPTION

Figure 1:
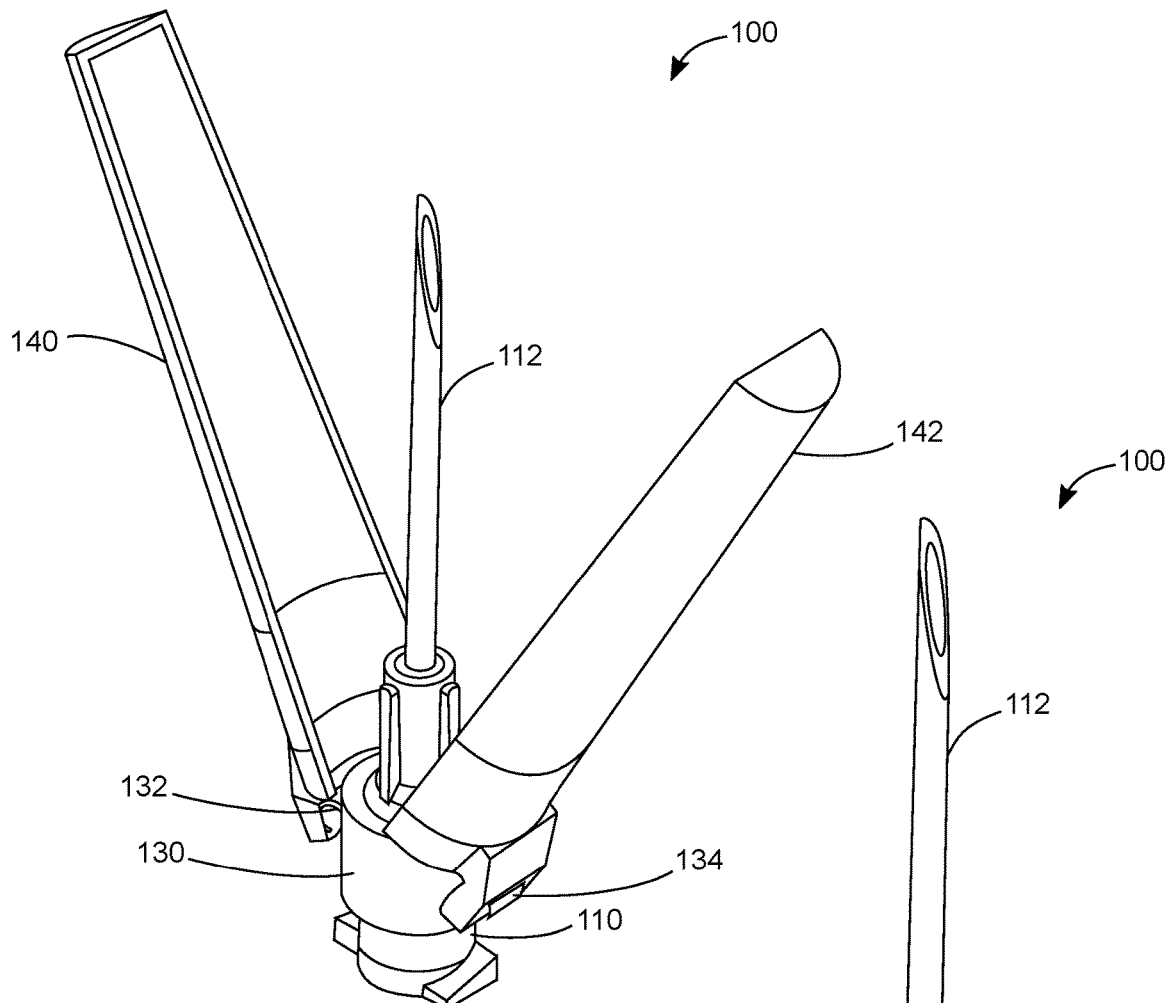
FIG. 1 illustrates a perspective view of a safety needle device according to an exemplary first embodiment of the present disclosure.

Embodiments of the disclosure aims to provide a safety mechanism incorporating features of both needle shields and safety shield mechanisms, reducing material costs, manufacturing complexity and waste.

Embodiments of the disclosure pertain to a safety needle device for connection to a medical connector, including threaded connections. In one or more embodiments, the safety needle comprises a collar configured to interdigitate with a conventional needle hub, the collar having attachment points for a hinged cap, the hinged cap being in a two-piece configuration. In further embodiments, the safety needle device comprises a removable hard needle cover configured to cover needle cannula and a distal portion of a needle hub. The hard needle enclosure further comprises a cap configured to interdigitate with the needle cover and cover a proximal portion of the needle hub. The cap and at least a portion of the needle cover are covered by a removable sleeve which holds the cap and the needle cover together. Even further embodiments comprise a needle hub, a needle cover, an adapter and a cap, the adapter configured to attach to a conventional needle cap. The disclosure aims to provide a safety mechanism incorporating features of both needle shields and safety shield mechanisms, reducing material costs, manufacturing complexity and waste.

Other embodiments of the disclosure pertain to hard-packaged needle devices including a hard needle enclosure. In one or more embodiments, the needle for blister packaging is eliminated because the hard needle enclosure provides sterile packaging of the needle.

Before describing several exemplary embodiments of the disclosure, it is to be understood that the disclosure is not limited to the details of construction or process steps set forth in the following description. The disclosure is capable of other embodiments and of being practiced or being carried out in various ways.

For purposes of the description hereinafter, the terms "top", "bottom", "longitudinal", and derivatives thereof shall relate to the disclosure as it is oriented in the drawing figures. However, it is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

As used herein, the use of "a," "an," and "the" includes the singular and plural.

As used herein, the term "Luer connector" refers to a connection collar that is the standard way of attaching syringes, catheters, hubbed needles, IV tubes, etc. to each other. The Luer connector consists of one or more interlocking tubes, slightly tapered to hold together with just a simple pressure/twist fit/friction fit. Luer connectors can optionally include an additional outer rim of threading, allowing them to be more secure. The Luer connector can interlock and connect to the end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe. As used herein, the term "Luer connector" refers to a male luer connector or a female luer connector.

As used herein, the term "medical device" refers to common medical devices having threaded or interlocking connections, the connections having corresponding mating elements. By way of example but not limitation, a syringe may have a threaded connection which releasably interlocks with a secondary medical device such as a needless connector of a catheter, an IV line and the like. The threaded connection may include a lumen defining a fluid path surrounded by a protruding wall having the threaded means for attaching to the secondary medical device.

As would be readily appreciated by skilled artisans in the relevant art, while descriptive terms such as "thread", "taper", "tab", "wall", "top", "side", "bottom" and others are used throughout this specification to facilitate understanding, it is not intended to limit any components that can be used in combinations or individually to implement various aspects of the embodiments of the present disclosure.

A first embodiment of the safety needle device comprises a removable collar configured to interdigitate with a conventional needle hub, the collar having attachment points for a hinged cap, the hinged cap being in a two-piece configuration which fold to cover a needle cannula of the needle hub. In one or more embodiments, the collar and the two-piece hinged cap are configured as a shield assembly that may be fitted to conventional needle hubs and may be packaged separately. In one or more embodiments, the two-piece hinged cap is configured as a re-use prevention mechanism by irreversibly snapping together after use of the needle. In one or more embodiments, the collar is configured to freely rotate around the needle hub, thereby allowing a practitioner to move the two-piece hinged cap out of the field of view or away from the insertion site. In further embodiments, the safety needle device comprises a removable hard needle cover configured to cover needle cannula and a distal portion of a needle hub. The hard needle enclosure further comprises a cap configured to interdigitate with the needle cover and cover a proximal portion of the needle hub. The cap and at least a portion of the needle cover are covered by a removable sleeve which holds the cap and the needle cover together. Even further embodiments comprise a needle hub, a needle cover, an adapter and a cap, the adapter configured to attach to a conventional needle cap. In an exemplary implementation of the embodiments of present disclosure, the disinfection cap includes integrated threads or tabs, and other features in any and all combinations allowing it to interface with a threaded fitting of a medical device. In preferred embodiments, the disinfection cap interfaces with a Luer fitting. Exemplary configurations for couplers, fittings, ports and adapters may include commercially available luer locks, luer slip ports, locking ports, threaded connections, interlocking connection or generally other common medical device fitting known in the art.

Referring now to the drawings, wherein like reference numerals designate identical or corresponding parts throughout the several views, embodiments of the present disclosure are described as follows.

As depicted in FIG. 1, a first embodiment of the safety needle device 100 comprises a removable collar 130 configured to interdigitate with a needle hub 110, the collar 130 having two attachment points (132, 134) for a two-piece hinged cap (140, 142). The hub 110 is configured to couple to a syringe. The two-piece hinged cap (140, 142) is configured to fold over and cover a needle cannula 112 of the needle hub 110. In one or more embodiments, the two-piece hinged cap (140, 142) is configured as a re-use prevention mechanism by irreversibly snapping together after use of the needle cannula 112. In one or more embodiments, the two-piece hinged cap (140, 142) is configured as a shield assembly that may be fitted to conventional needle hubs and may be packaged separately. In one or more embodiments, the collar 130 is configured to freely rotate around the needle hub 110, thereby allowing a practitioner to move the two-piece hinged cap (140, 142) out of the field of view or away from the insertion site. In one or more embodiments, the collar 130 is configured to non-removably interdigitate with the needle hub 110 to prevent removal of the collar 130.

Figure 2:
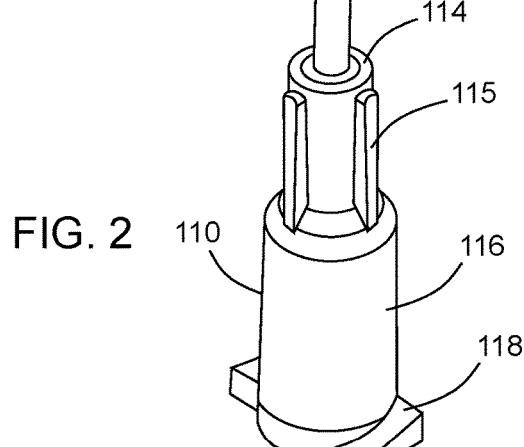
FIG. 2 illustrates a perspective view of a needle hub of the safety needle device of the first embodiment.

As shown in FIG. 2, the needle hub 110 comprises a cylindrical body having a distal portion 114 and a proximal portion 116. From the distal portion 114 extends a needle cannula 112 in a distal direction. In one or more embodiments, the distal portion 114 further includes a plurality of longitudinal ribs 115. The proximal portion 116 has a substantially cylindrical shape. In one or more embodiments, the proximal portion 116 tapers in a distal direction. The proximal portion 116 further comprises a cavity in fluid communication with the lumen, the cavity being configured to receive a hub of a luer connector. In one or more embodiments, the cavity can be configured to facilitate a loose fit between the cavity and the hub of the luer connector, wherein the needle hub 110 is secured by an at least one thread 118 or set of tabs included on an outer surface of the proximal portion 116. The at least one thread 118 is sized and to have a thread pattern that will engage with a standard ISO-2 type of luer fitting. In further embodiments, the cavity can be configured in a Luer Slip fitting to facilitate an interference fit between the cavity and the hub of the luer connector. In one or more embodiments, the interference fit can be configured to be sufficiently strong enough to not require a threaded connection or the at least one thread 118 in removably securing the cavity to the luer connector. In one or more embodiments, the at least one thread 118 can include an inclined thread pattern. In one or more embodiments, the at least one thread 118 can include a helical-shaped thread pattern. Such connectors are generally and commonly used as catheter and other fluid-tight protective connectors in medical applications. Further alternate embodiments are non-removably or removably assembled with a threaded connection, press-fit connection, adhesive connection or a combination thereof.

Figure 3:
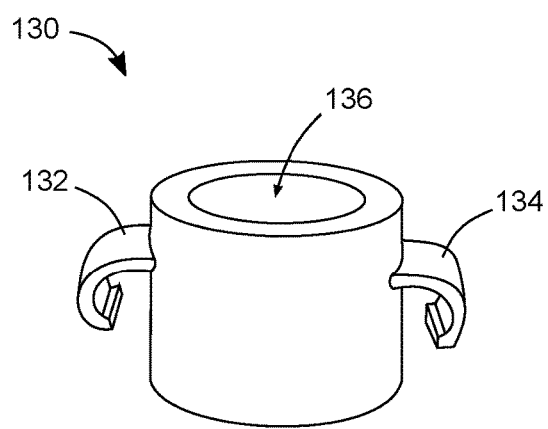
FIG. 3 illustrates a perspective view of a collar of the safety needle device of the first embodiment.

As shown in FIG. 3, the removable collar 130 comprises a substantially cylindrical body having an aperture 136 extending therethrough. The aperture 136 is sized and configured to receive the proximal portion 116 of the needle hub 110. In one or more embodiments, the aperture 136 is sized and configured to create an interference fit with the proximal portion 116 of the needle hub 110. In one or more embodiments, the aperture 136 is sized and configured to create a loose fit with the proximal portion 116 of the needle hub 110. In one or more embodiments, the collar 130 freely rotates around the proximal portion 116 of the needle hub 110. In one or more embodiments, the collar 130 is configured to snap into the needle hub 110, whereby the collar 130 is able to freely rotate, but not able to move in a longitudinal direction, and is thus not removable from the needle hub 110. In one or more embodiments, the collar 130 can be removed upon sufficient application of force, the force being greater than forces normally exhibited upon said devices, thereby preventing inadvertent removal. In one or more embodiments, the collar 130 is configured to snap into the needle hub 110 creating an interference fit, whereby the collar 130 is able to freely rotate only upon application of sufficient force, thereby resisting free movement.

The collar 130 further comprises two attachment points (132, 134) disposed on an outer surface of the collar 130, each of the two attachment points (132, 134) being configured to attach to each of the two-piece hinged cap (140, 142). In one or more embodiments, the two attachment points (132, 134) are disposed 180 degrees from one another. In one or more embodiments, the two attachment points (132, 134) protrude from the outer surface of the collar 130 and are in the form of hooks, each hook being configured to the hooks being configured to receive loops (144, 146) of the two-piece hinged cap (140, 142). The two attachment points (132, 134) are sized and shaped to create a snap fit with the loops (144. 146) of the two-piece hinged cap (140, 142) In one or more embodiments, the two attachment points (132, 134) protrude from the outer surface of the collar 130 and are in the form of loops, each loop being configured to interdigitate with hooks of the two-piece hinged cap (140, 142). In one or more embodiments, the two attachment points (132, 134) and loops (144. 146) also create an interference fit, whereby the two attachment points (132, 134) are able to freely rotate only upon application of sufficient force, thereby resisting free movement.

In one or more embodiments, the collar 130 and the two-piece hinged cap (140, 142) are integrally formed. In one or more embodiments, the collar 130 and the two-piece hinged cap (140, 142) are integrally formed, the two attachment points (132, 134) being configured as a living hinge. In one or more embodiments, the two attachment points (132, 134) are configured as a living hinge having a residual spring action, wherein the living hinge is in an open state in its resting position. The open state of the living hinge resists movement of the two-piece hinged cap (140, 142), keeping the two two-piece hinged cap (140, 142) away from the insertion site.

Figure 4:
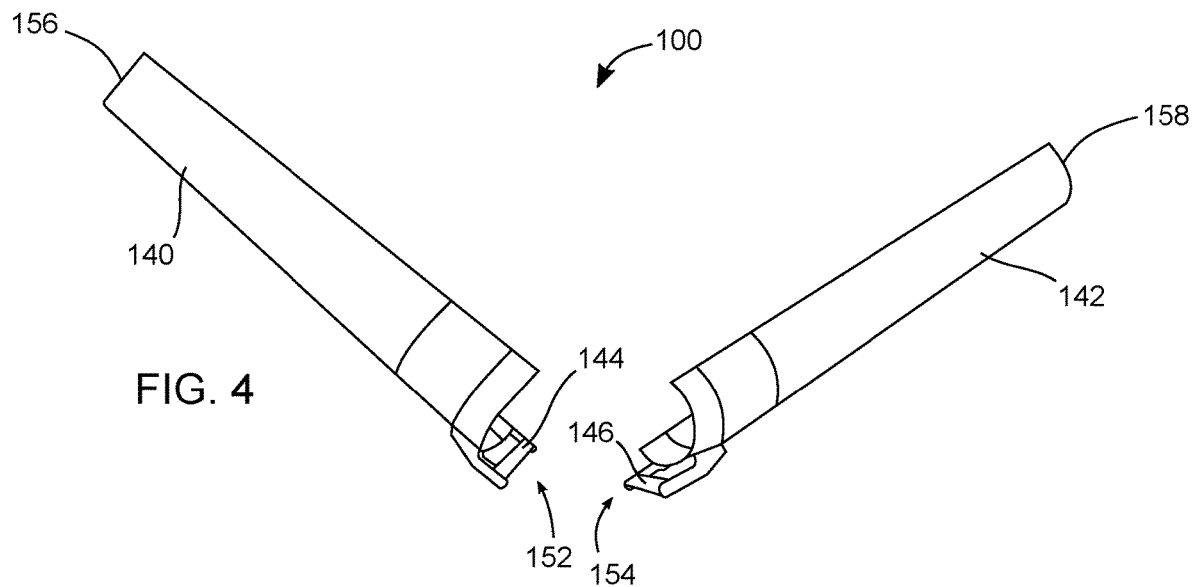
FIG. 4 illustrates a perspective view of a cap of the safety needle device of the first embodiment.

As shown in FIG. 4, each of the pieces of the two-piece hinged cap (140, 142) comprises elongated bodies having a semicircular cross-section. Each of the two elongated bodies have a cavity (148, 150) defined by an open proximal end (152, 154) and a closed distal end (156, 158). From the open proximal ends (152, 154) extend loops (144, 146) configured to interdigitate with the two attachment points (132, 134) disposed on the outer surface of the collar 130. The two-piece hinged cap (140, 142) is configured as a clamshell configuration, in which each of the elongated bodies are configured to close in on one another, providing for a closed cavity in which the needle cannula 112 is protected. In one or more embodiments, the elongated bodies snap together upon full closure. In one or more embodiments, each of the two-piece hinged cap (140, 142) are identical to one another. In one or more embodiments, each of the two-piece hinged cap (140, 142) are configured to be manufactured or shot from the same mold, thus reducing manufacturing costs due to simplification of the molding.

Figure 5:
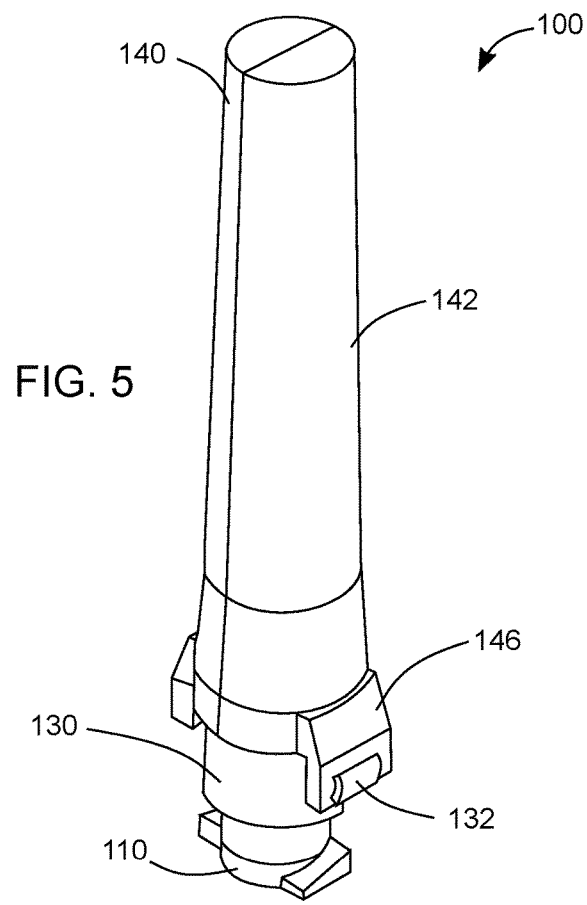
FIG. 5 illustrates a perspective view of the safety needle device of the first embodiment in a closed state.

In one or more embodiments, as shown in FIG. 5, the safety needle device 100 is packaged and supplied to medical practitioners in a closed state. In one or more embodiments, the safety needle device 100 is packaged within blister packaging to maintain sterility. In the closed state, the two-piece hinged cap (140, 142) is reversibly closed onto itself. In one or more embodiments, the two-piece hinged cap (140, 142) is held closed by a disposable plastic seal or sleeve disposed over the two-piece hinged cap (140, 142). In one or more embodiments, the disposable seal or sleeve is loosely fit over the two-piece hinged cap (140, 142). In one or more embodiments, the disposable plastic seal or sleeve has perforations or break points configured to break open upon pulling apart the two-piece hinged cap (140, 142). In one or more embodiments, the disposable plastic seal or sleeve has a pull tab configured to separate the disposable plastic seal or sleeve upon application of force away from the two-piece hinged cap (140, 142). In one or more embodiments, the disposable plastic seal or sleeve is sealed with an adhesive that is weak enough to separate upon application of force away from the two-piece hinged cap (140, 142).

As shown in FIG. 5, the assembled safety needle device 100 is in an open state, in which the two-piece hinged cap (140, 142) is freely able to open or close or move and the collar 130 is freely able to rotate around the needle hub 110. In the open state, the needle cannula 112 is fully exposed and may be inserted into the skin of a patient. Due to the free movement of the two-piece hinged cap (140, 142) and the collar 130 with respect to the needle hub 110, the practitioner is able to rotate or move the two-piece hinged cap (140, 142) away from the insertion site or out of the field of view of the practitioner. In the open state, the two-piece hinged cap (140, 142) is movable from 0 degrees with respect to the cannula 112 to at least 170 degrees with respect to the needle cannula 112. In one or more embodiments, the two-piece hinged cap (140, 142) is movable from 0 degrees with respect to the cannula 112 to at least 150 degrees with respect to the needle cannula 112. In one or more embodiments, the two-piece hinged cap (140, 142) is movable from 0 degrees with respect to the cannula 112 to at least 125 degrees with respect to the needle cannula 112. In one or more embodiments, the two-piece hinged cap (140, 142) is movable from 0 degrees with respect to the cannula 112 to approximately 170 degrees with respect to the needle cannula 112.

Throughout the full range of motion the practitioner is able to either rotate or move the two-piece hinged cap (140, 142) away from a barrel of a syringe whereby the practitioner has a clear view of markings disposed on the barrel of the syringe to ensure that a correct dosage is metered. In one or more embodiments, each of the two-piece hinged cap (140, 142) is freely able to open or close independently, wherein one of the two-piece hinged cap (140, 142) is movable independent from the other of the one of the two-piece hinged cap (140, 142).

Figure 6:
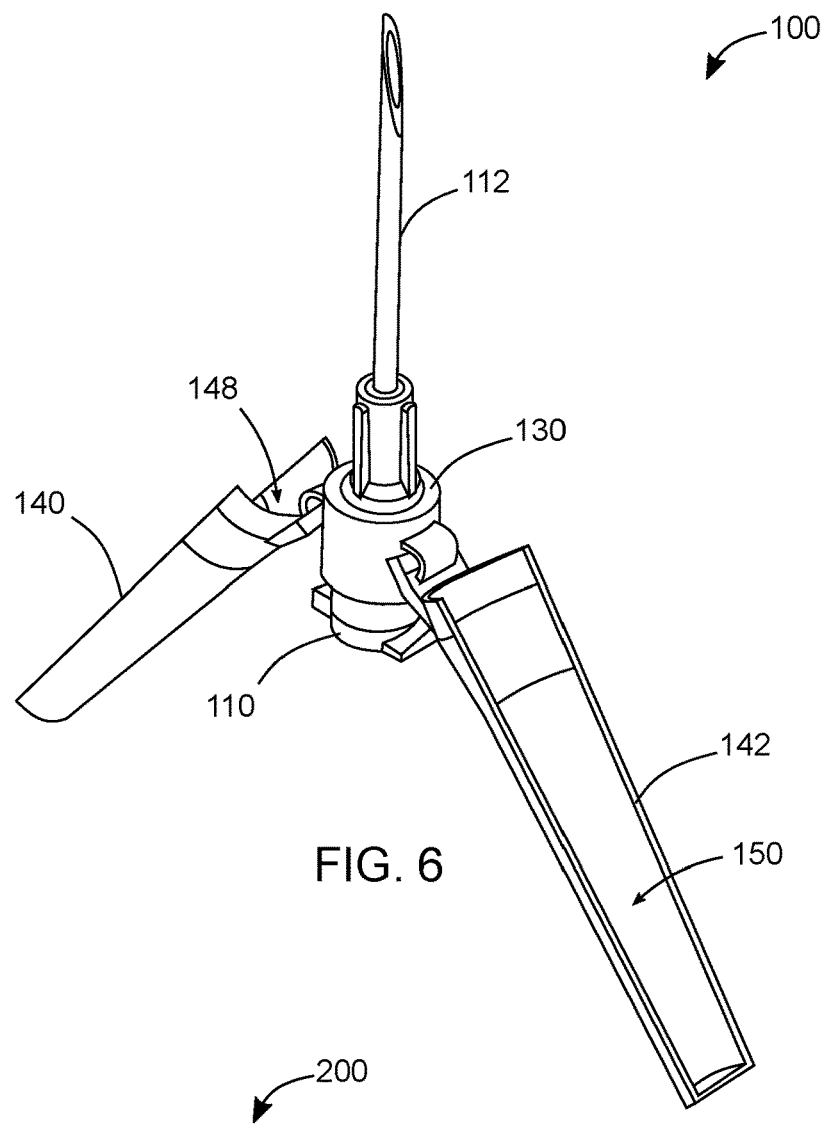
FIG. 6 illustrates a perspective view of the safety needle device of the first embodiment in an open state.

As shown in FIGS. 5 and 6, upon administration of the medical treatment, the practitioner may close the two-piece hinged cap (140, 142) onto itself to bring the safety needle device 100 to a final closed state. This action may be performed with the same hand used to administer the medical treatment or the opposite hand. Due to the two-piece hinged cap (140, 142) closing in a snap-fitment, pressure to the two-piece hinged cap (140, 142) is sufficient to close the two-piece hinged cap (140, 142). In one or more embodiments, the closed distal ends (156, 158) of the two-piece hinged cap (140, 142) are configured to non-removably lock upon closure of the two-piece hinged cap (140, 142) in the final closed state, thereby preventing reuse of the safety needle device 100. The safety needle device 100 in the final closed state may then be disposed in accordance with conventional biohazard waste practices.

In an alternative embodiment, a sleeve may be disposed over the two-piece hinged cap (140, 142) in the closed state. The sleeve can move up and down in a longitudinal direction over two-piece hinged cap (140, 142) and in doing so, push the two-piece hinged cap (140, 142) together or pull the two-piece hinged cap (140, 142) apart, or alternatively, permit the two-piece hinged cap (140, 142) to come apart. In one or more embodiments, the two-piece hinged cap (140, 142) is molded having a living hinge with a residual spring action. In one or more embodiments, the sleeve locks the two-piece hinged cap (140, 142).

Figure 7:
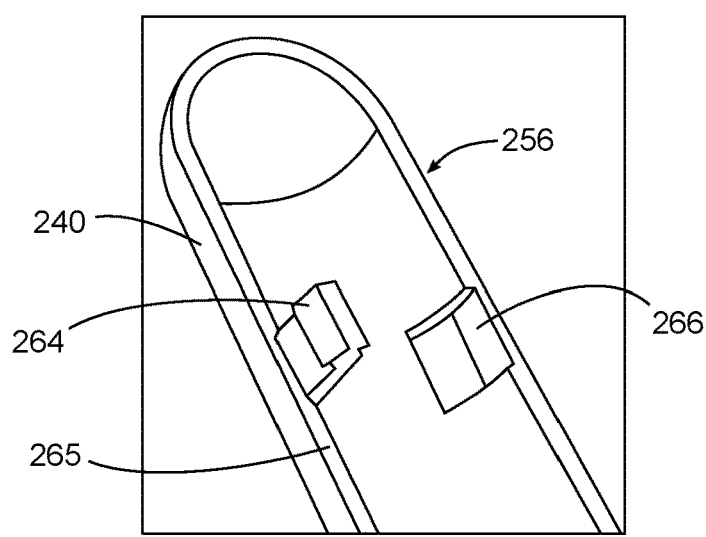
FIG. 7 illustrates a detailed view of a locking mechanism of a safety needle device of a second embodiment.
Figure 8:
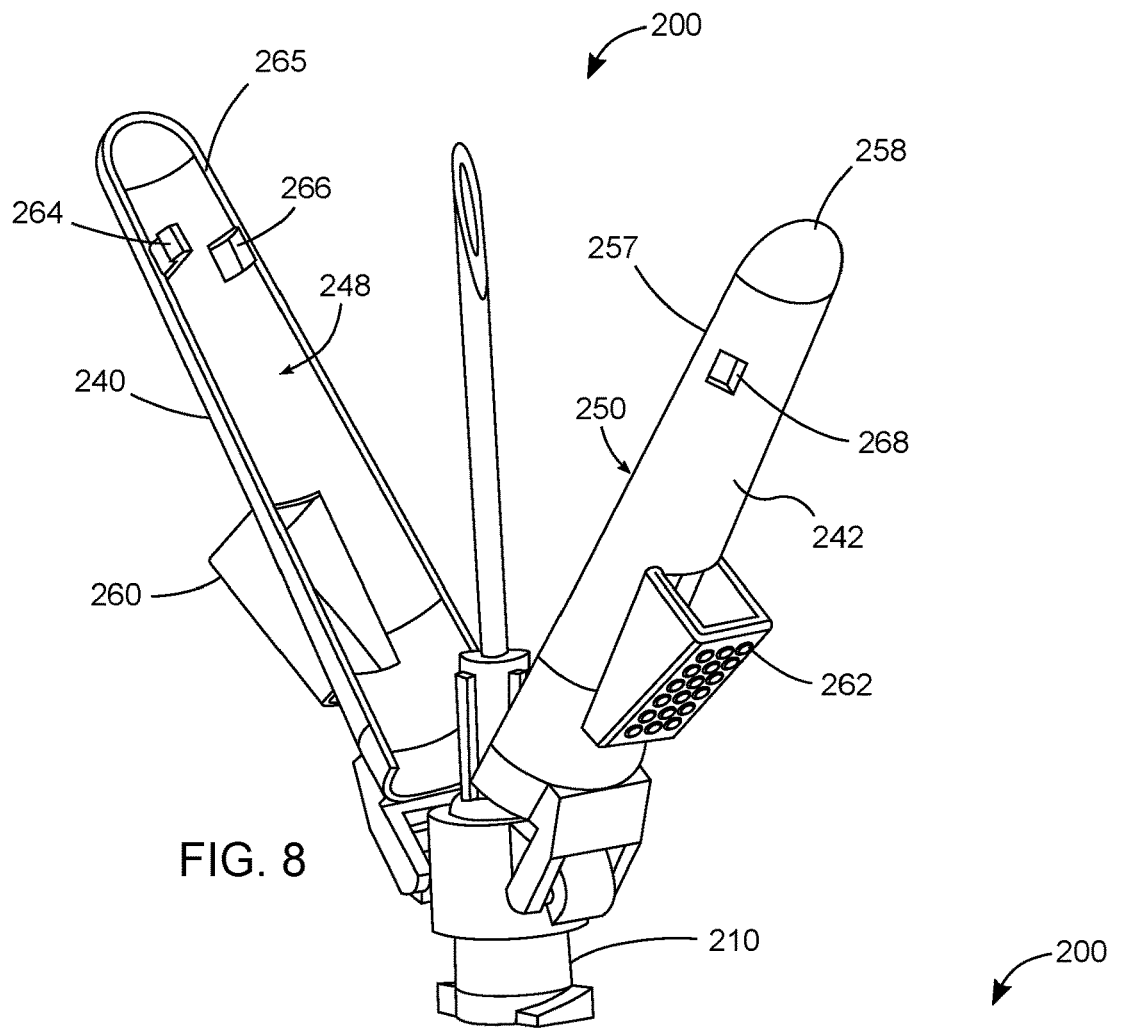
FIG. 8 illustrates a side view of the safety needle device of the second embodiment in an open state.
Figure 9:
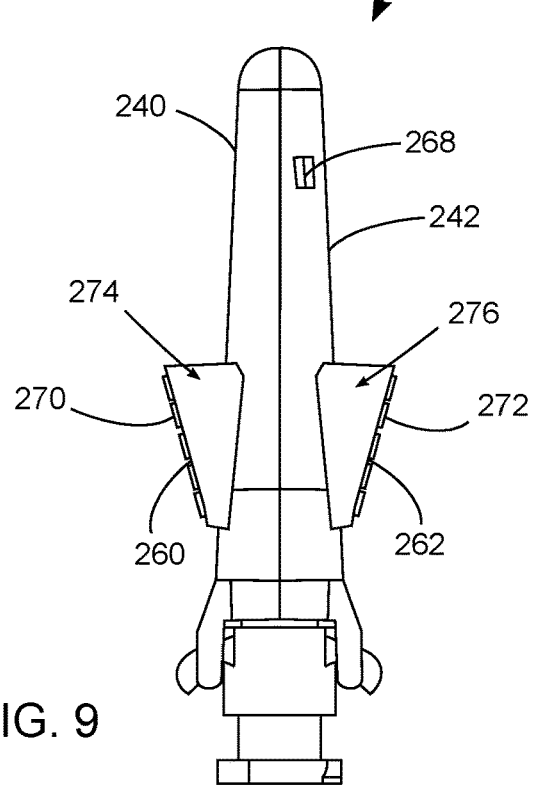
FIG. 9 illustrates a side view of the safety needle device of the second embodiment in a closed state.

A second embodiment of the present disclosure is shown in FIGS. 7-9, the second embodiment incorporating the elements of embodiments disclosed herein. A two-piece hinged cap (240, 242) of a safety needle device 200 further comprises a locking mechanism disposed a distance from a closed distal end (256, 258) of the two-piece hinged cap (240, 242). The locking mechanism comprises a hook tab 264 projecting from an edge 265 of one of the two-piece hinged cap (240, 242) and a corresponding aperture 268 disposed within the cavity 250 of the other of the two-piece hinged cap (240, 242), the aperture 268 configured to interdigitate and removably or non-removably receive the hook tab 264. In one or more embodiments, one of the two-piece hinged cap (240, 242) further comprises an aperture 266 disposed within a cavity 248 of the of one of the two-piece hinged cap (240, 242) and a corresponding hook tab 269 projecting from an edge 257 of the other of the two-piece hinged cap (240, 242), the aperture 268 being configured to interdigitate and removably or non-removably receive the hook tab 269.

As shown in FIG. 9, the hook tab 264 being received within the corresponding aperture 268 and the hook tab 269 being received within the corresponding aperture 268 removably or non-removably lock the two-piece hinged cap (240, 242) together. In one or more embodiments, the locking mechanism is configured to non-removably lock upon closure of the two-piece hinged cap (240, 242) in the final closed state, thereby preventing reuse of the safety needle device 200. The safety needle device 200 in the final closed state may then be disposed in accordance with conventional biohazard waste practices.

As shown in FIGS. 8 through 11, in one or more embodiments, each of the two-piece hinged cap (240, 242) of the safety needle device 200 further comprises push features (260, 262) configured to abut a barrel surface of a syringe when a needle hub 210 is connected to a luer connector of the syringe and in an open state. The push features (260, 262) are disposed on the elongated bodies of the two-piece hinged cap (240, 242). In one or more embodiments, the push features (260, 262) have a triangular shape, the triangular shape having a hypotenuse face (270, 272) configured to abut the barrel surface of the syringe when a needle hub 210 is connected to the luer connector of the syringe while in the open state, and a right face (274, 276), the right face (274, 276) being at a right angle with the surfaces of the elongated bodies of the two-piece hinged cap (240, 242). In one or more embodiments, the push features (260, 262) are configured as grip features for aiding in manipulating the two-piece hinged cap (240, 242).

Figure 10:
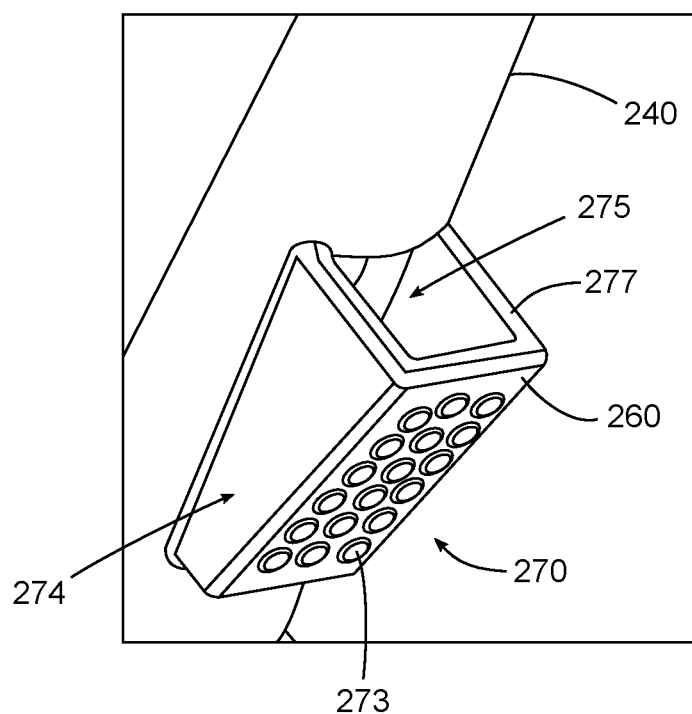
FIG. 10 illustrates a detailed side view of the safety needle device of the second embodiment.

In one or more embodiments, as shown in FIG. 10, the hypotenuse face (270, 272) further includes a textured or hatched surface 273. The textured or hatched surface 273 aids in manipulation of the two-piece hinged cap (240, 242). In one or more embodiments, the hypotenuse face (270, 272) aids in pushing the two-piece hinged cap (240, 242) together. In one or more embodiments, the right face (274, 276) further includes an aperture 275 extending through the right face (274, 276). An edge 277 formed by the aperture 275 and the hypotenuse face (270, 272) is configured to allow or aid the practitioner to pull the two-piece hinged cap (240, 242) apart.

Figure 11A:
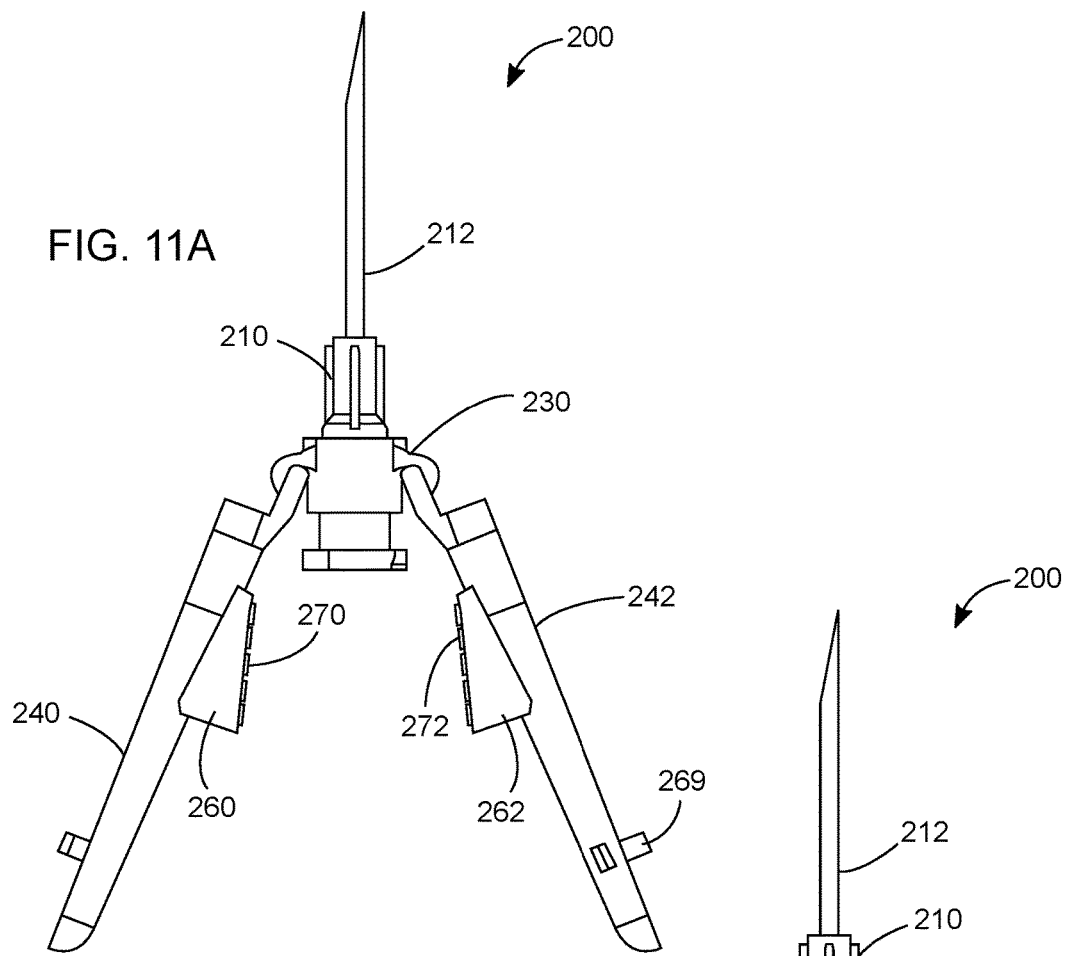
FIG. 11A illustrates a side view of the safety needle device of the second embodiment in the open state.

As shown in FIG. 11A, the safety needle device 200 is in a fully open state, wherein the hypotenuse face (270, 272) abuts the barrel surface of a syringe. In the fully open state, the two-piece hinged cap (240, 242) is freely able to open or close or move and the collar 230 is freely able to rotate around the needle hub 210. In the fully open state, the two-piece hinged cap (240, 242) is movable from 0 degrees with respect to the cannula 212 to at least 175 degrees with respect to the needle cannula 212. Throughout the full range of motion the practitioner is able to either rotate or move the two-piece hinged cap (240, 242) away from a barrel of the syringe whereby the practitioner has a clear view of markings disposed on the barrel of the syringe to ensure that a correct dosage is metered.

Figure 11B:
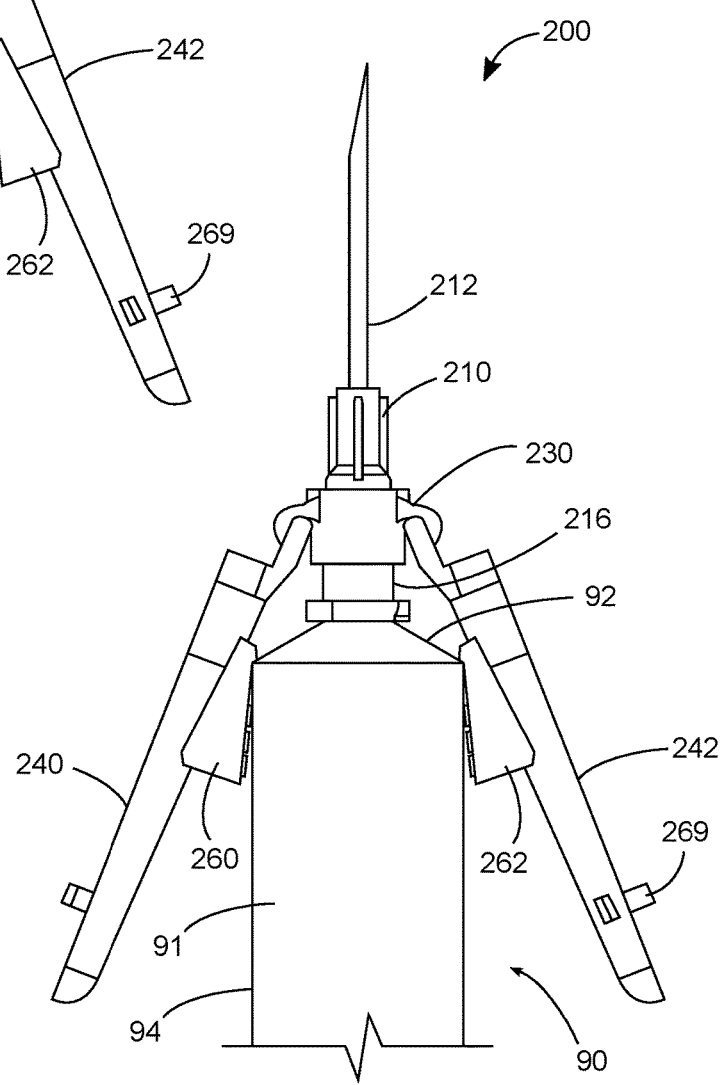
FIG. 11B illustrates a side view of the safety needle device of the second embodiment in the open state, the safety needle device attached to a syringe barrel.

As shown in FIG. 11B, the safety needle device 200 is in the fully opened state and attached to a syringe barrel 90. The syringe barrel 90 comprises an elongated cylindrical body 91 having an open proximal end (not shown) and a distal end 92 defining a cavity for retaining fluids. The cylindrical body 91 has an outside cylindrical surface 94, which in some embodiments, has markings or fluid volume indicators.

A proximal portion 216 of the needle hub 110 is inserted over an elongated tip (not shown) disposed on the distal end 92 of the barrel 90, securing the needle hub 110 on the elongated tip. In the fully opened state, the hypotenuse face (270, 272) abuts the outside cylindrical surface 94 of the syringe barrel 90 creating a hard stop for the range of motion of the two-piece hinged cap (240, 242). As shown, the two-piece hinged cap (240, 242) in the fully opened state is at angle of 170 degrees with respect to the cannula 212 whereby the hypotenuse face (270, 272) abuts the outside cylindrical surface 94 of the syringe barrel 90. As shown, in the fully opened state, the needle cannula 212 is fully exposed and unobstructed, allowing a practitioner to have a full view of the needle cannula 212 being inserted into an insertion site of the patient's skin.

In one or more embodiments, in the fully open state, the two-piece hinged cap (240, 242) is movable from 0 degrees with respect to the cannula 212 to at least 175 degrees with respect to the needle cannula 212. In one or more embodiments, in the fully open state, the two-piece hinged cap (240, 242) is movable from 0 degrees with respect to the cannula 212 to at least 165 degrees with respect to the needle cannula 212. In one or more embodiments, in the fully open state, the two-piece hinged cap (240, 242) is movable from 0 degrees with respect to the cannula 212 to at least 160 degrees with respect to the needle cannula 212.

Figure 12:
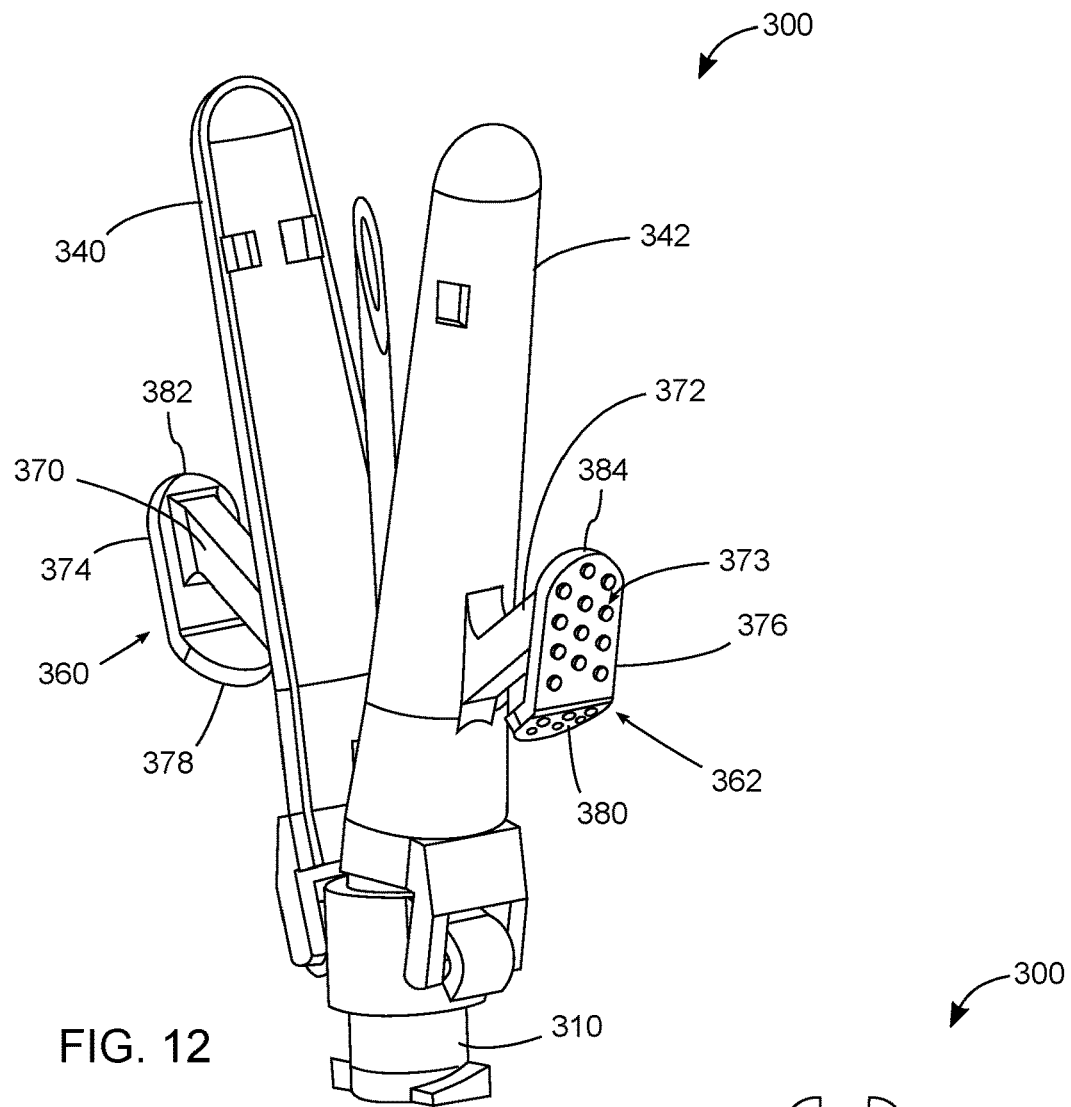
FIG. 12 illustrates a side view of the safety needle device of a third embodiment in an open state.
Figure 13:
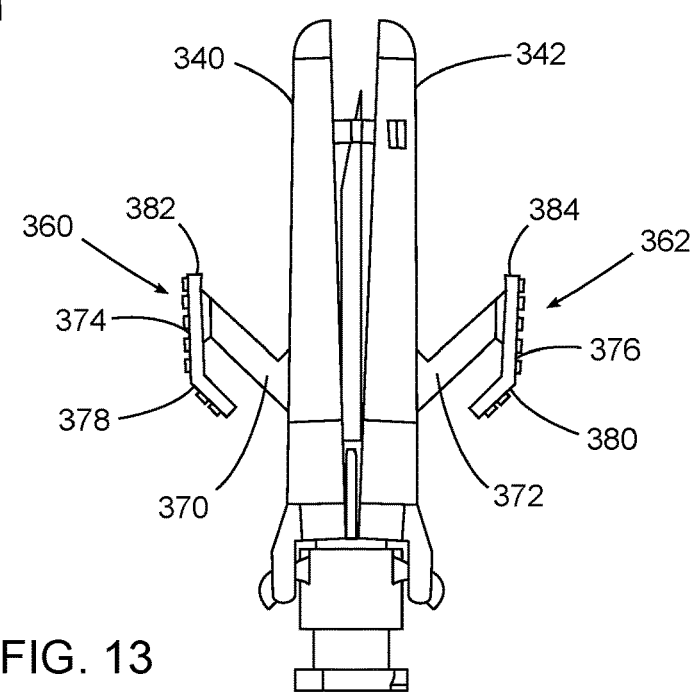
FIG. 13 illustrates a side view of the safety needle device of the third embodiment in the open state.
Figure 14:
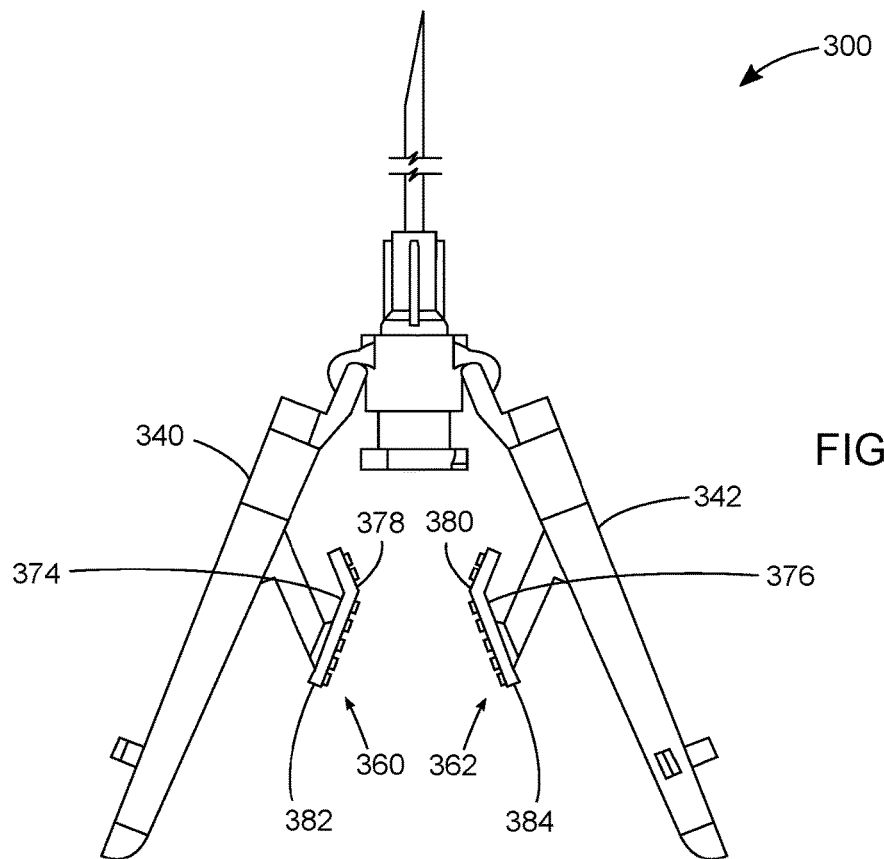
FIG. 14 illustrates a side view of the safety needle device of the third embodiment in the open state.

As shown in FIGS. 12-14, a third embodiment is described, the third embodiment incorporating the elements of embodiments disclosed herein. Each of a two-piece hinged cap (340, 342) of a safety needle device 300 further comprises push features (360, 362) configured to abut a barrel surface of a syringe when a needle hub 310 is connected to a luer connector of the syringe and in an open state. The push features (360, 362) are disposed on the elongated bodies of the two-piece hinged cap (340, 342). In one or more embodiments, the push features (360, 362) are configured as tabs protruding from the elongated bodies of the two-piece hinged cap (340, 342). Each of the tabs having a neck (370, 372), a thumb press surface (374, 376) and a barrel engaging surface (378. 380). The barrel engaging surface (378. 380) is configured to abut the barrel surface of the syringe when a needle hub 310 is connected to the luer connector of the syringe while in the open state. The thumb press surface is (374, 376) is configured to aid in manipulating the two-piece hinged cap (340, 342). In one or more embodiments, thumb press surface is (374, 376) is configured to aid in pushing the two-piece hinged cap (340, 342) onto one another. In one or more embodiments, thumb press surface (374, 376) further includes a textured or hatched surface 373. The textured or hatched surface 373 aids in manipulation of the two-piece hinged cap (240, 242). A distal edge (382, 384) of the thumb press surface is (374, 376) is configured to aid in manipulation of the two-piece hinged cap (240, 242). In one or more embodiments, the distal edge (382, 384) is configured to allow the practitioner to pull the two-piece hinged cap (340, 342) apart.

As shown in FIGS. 12-14, a third embodiment is described, the third embodiment incorporating the elements of embodiments disclosed herein. Each of a two-piece hinged cap (340, 342) of a safety needle device 300 further comprises push features (360, 362) configured to abut a barrel surface of a syringe when a needle hub 310 is connected to a luer connector of the syringe and in an open state. The push features (360, 362) are disposed on the elongated bodies of the two-piece hinged cap (340, 342). In one or more embodiments, the push features (360, 362) are configured as tabs protruding from the elongated bodies of the two-piece hinged cap (340, 342). Each of the tabs having a neck (370, 372), a thumb press surface (374, 376) and a barrel engaging surface (378. 380). The thumb press surface (374, 376) is disposed on the neck (370, 372), the thumb press surface (374, 376) being substantially parallel to the two-piece hinged cap (340, 342), and the barrel engaging surface (378. 380) extends at an angle from the thumb press surface (374, 376. The barrel engaging surface (378. 380) is configured to abut the barrel surface of the syringe when a needle hub 310 is connected to the luer connector of the syringe while in the open state.

The thumb press surface is (374, 376) is configured to aid in manipulating the two-piece hinged cap (340, 342). In one or more embodiments, thumb press surface is (374, 376) is configured to aid in pushing the two-piece hinged cap (340, 342) onto one another. In one or more embodiments, thumb press surface (374, 376) further includes a textured or hatched surface 373. The textured or hatched surface 373 aids in manipulation of the two-piece hinged cap (340, 342). A distal edge (382, 384) of the thumb press surface is (374, 376) is configured to aid in manipulation of the two-piece hinged cap (340, 342). In one or more embodiments, the distal edge (382, 384) is configured to allow the practitioner to pull the two-piece hinged cap (340, 342) apart.

Figure 15:
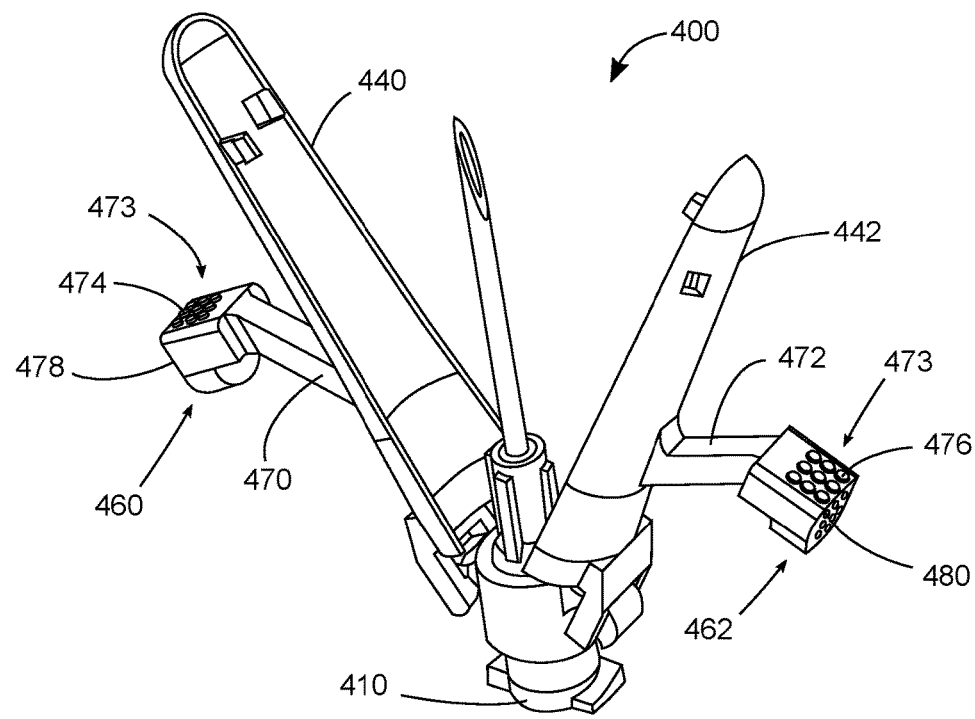
FIG. 15 illustrates a side view of the safety needle device of a fourth embodiment in an open state.
Figure 16:
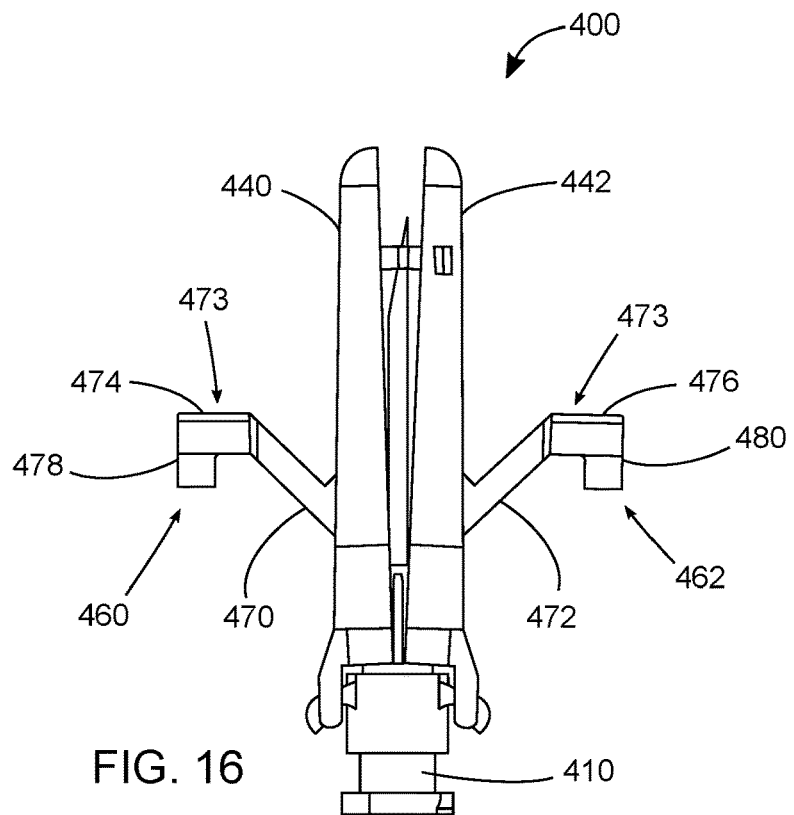
FIG. 16 illustrates a side view of the safety needle device of the fourth embodiment in the open state.
Figure 17:
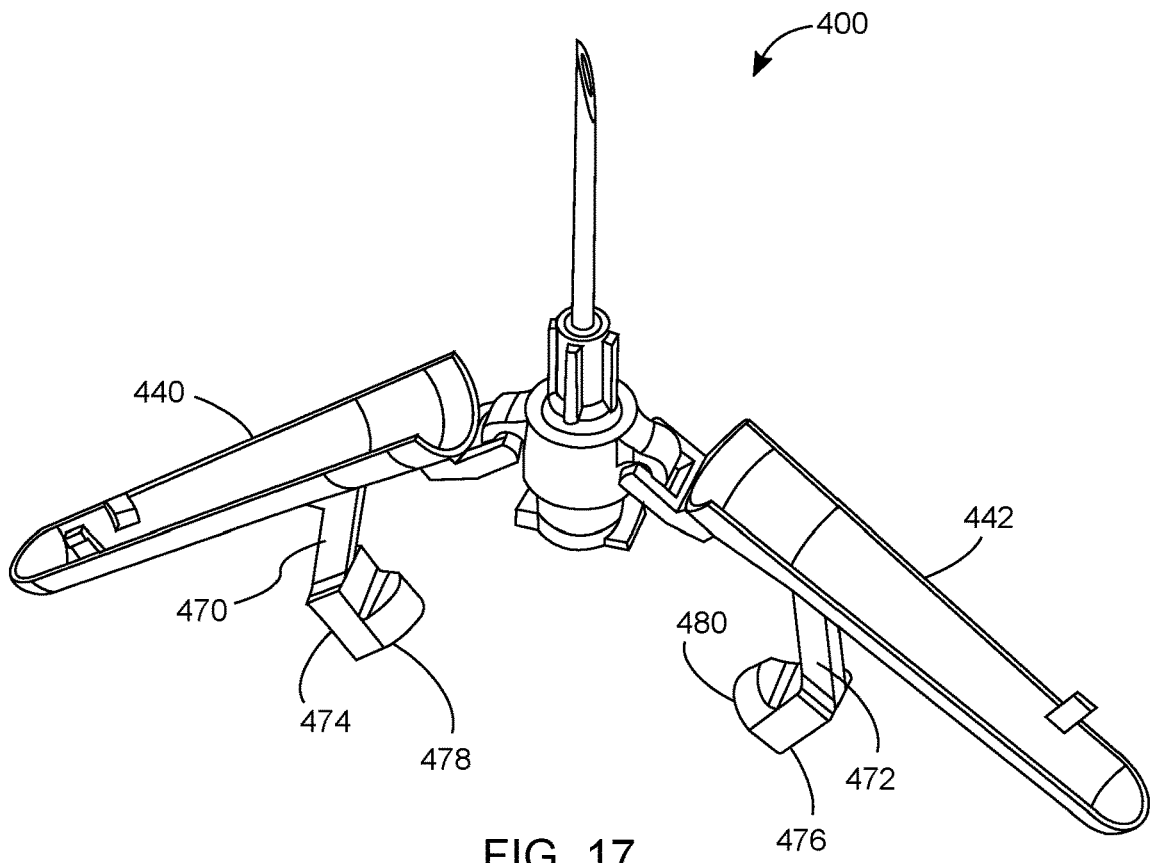
FIG. 17 illustrates a side view of the safety needle device of the fourth embodiment in the open state.

As shown in FIGS. 15-17, a fourth embodiment is described, the fourth embodiment incorporating the elements of embodiments disclosed herein. Each of a two-piece hinged cap (440, 442) of a safety needle device 400 further comprises push features (460, 462) configured to abut a barrel surface of a syringe when a needle hub 410 is connected to a luer connector of the syringe and in an open state. The push features (460, 462) are disposed on the elongated bodies of the two-piece hinged cap (440, 442). In one or more embodiments, the push features (460, 462) are configured as tabs protruding from the elongated bodies of the two-piece hinged cap (440, 442). Each of the tabs has a neck (470, 472), a thumb press surface (474, 476), and a barrel engaging surface (478. 480). The thumb press surface (474, 476) is disposed on the neck (470, 472), the thumb press surface (474, 476) being at a substantially right angle to the two-piece hinged cap (440, 442), and the barrel engaging surface (478. 480) extending at a right angle from the thumb press surface (474, 476). In one or more embodiments, the barrel engaging surface (478. 480) is substantially parallel to the two-piece hinged cap (440, 442). The barrel engaging surface (478. 480) is configured to abut the barrel surface of the syringe when a needle hub 410 is connected to the luer connector of the syringe while in the open state. The thumb press surface is (474, 476) is configured to aid in manipulating the two-piece hinged cap (440, 442).

In one or more embodiments, thumb press surface is (474, 476) is configured to aid in pushing the two-piece hinged cap (440, 442) onto one another. In one or more embodiments, the thumb press surface is (474, 476) is configured to allow the practitioner to pull the two-piece hinged cap (440, 442) apart. In one or more embodiments, thumb press surface (474, 476) further includes a textured or hatched surface 473. The textured or hatched surface 473 aids in manipulation of the two-piece hinged cap (440, 242).

Figure 18:
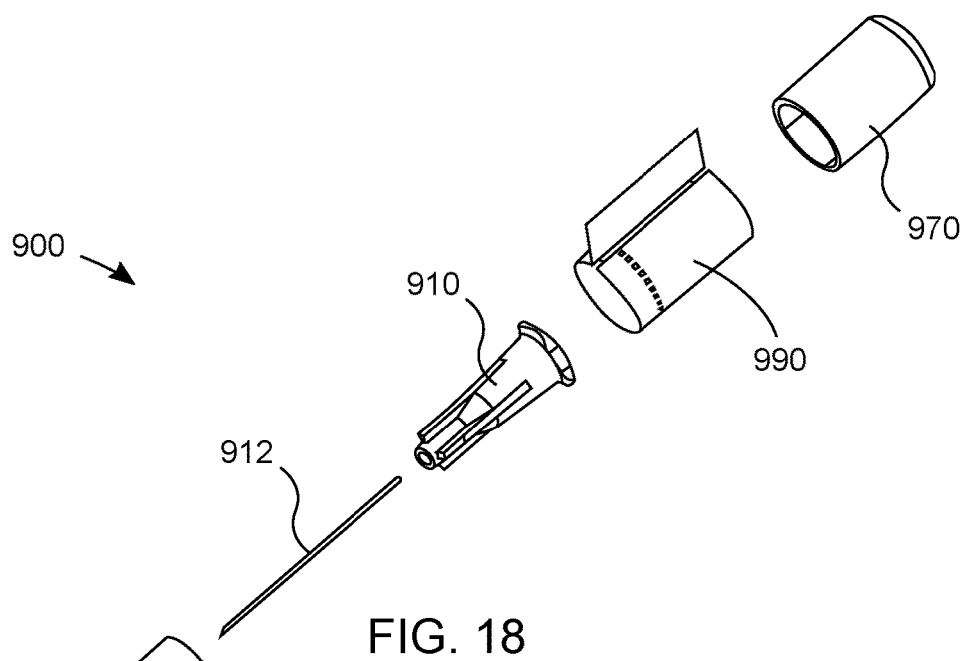
FIG. 18 illustrates an exploded view of a hard needle enclosure according to a second embodiment of the present disclosure.
Figure 19:
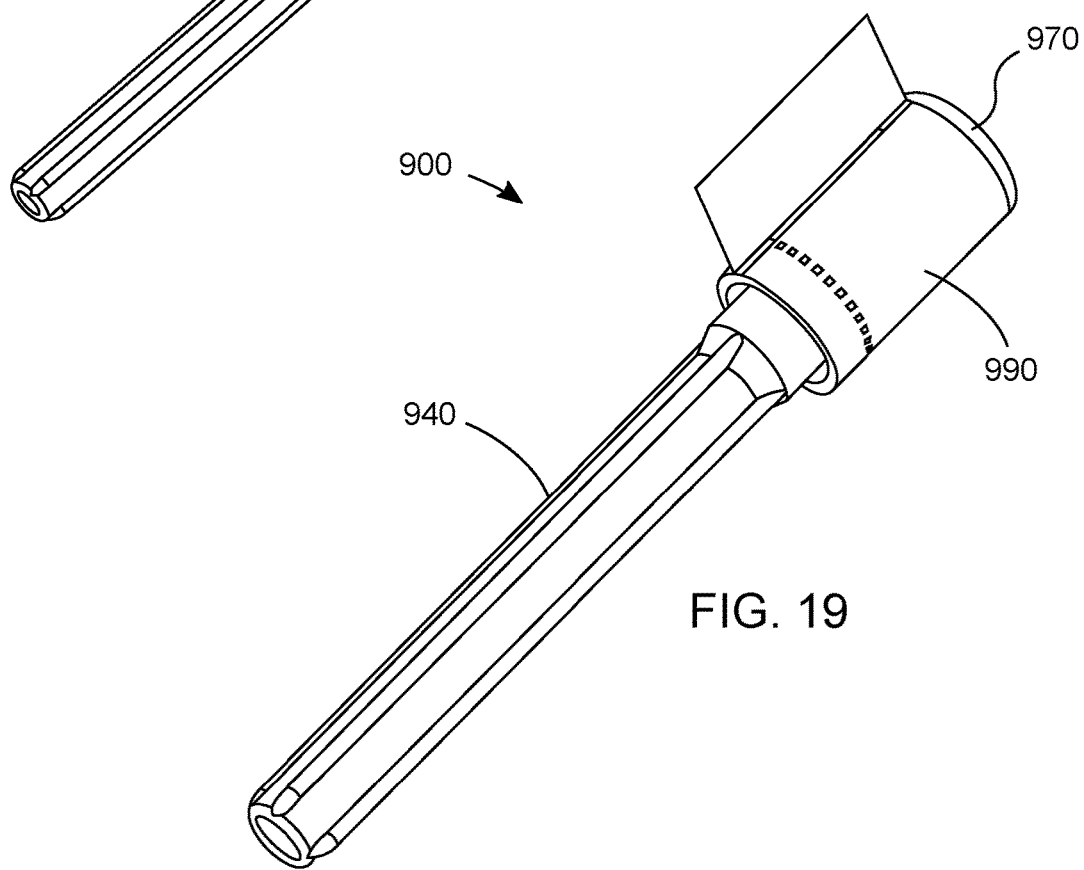
FIG. 19 illustrates an assembled view of the hard needle enclosure according to the second embodiment of the present disclosure.

As shown in FIGS. 18 and 19, a second embodiment of a safety needle device including a hard needle enclosure 900 comprises a removable hard needle cover 940 configured to cover needle cannula 912 and a distal portion 914 of a needle hub 910. The hard needle enclosure 900 further comprises a cap 970 configured to interdigitate with the needle cover 940 and cover a proximal portion 916 of the needle hub 910. The cap 970 and at least a portion of the needle cover 940 are covered by a removable sleeve 990 which holds the cap 970 and the needle cover 940 together.

Figure 20:
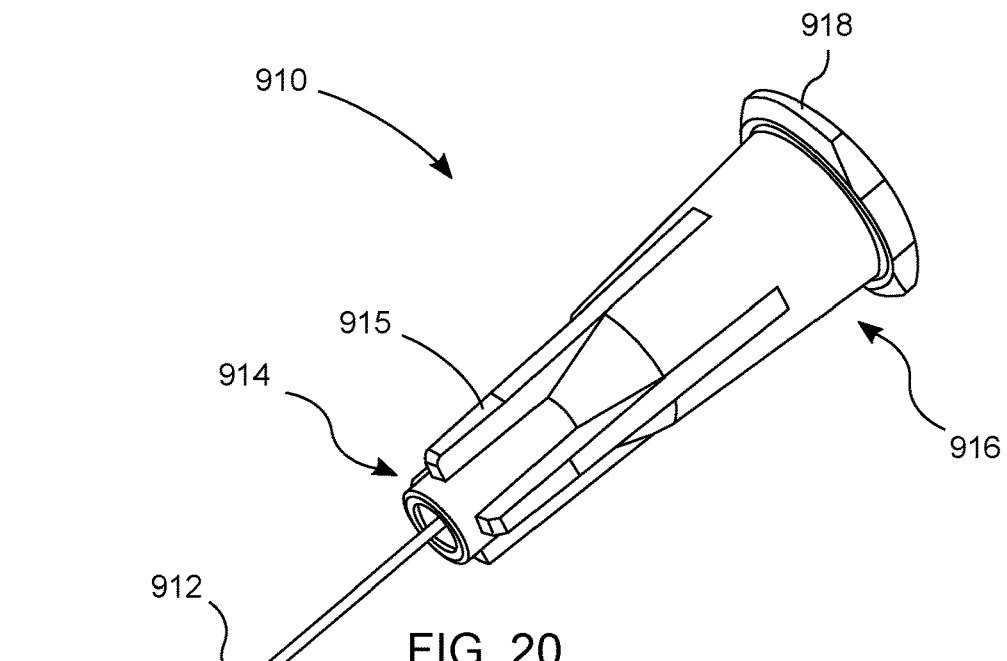
FIG. 20 illustrates a perspective view of a needle hub of the hard needle enclosure according to the second embodiment of the present disclosure.

As shown in FIG. 20, the needle hub 910 comprises a cylindrical body having a distal portion 914 and a proximal portion 916. From the distal portion 914 extends a needle cannula 912 in a distal direction, the needle cannula 912 being disposed in a lumen extending the length of the cylindrical body. In one or more embodiments, the distal portion 914 further includes a plurality of longitudinal ribs 915. The proximal portion 916 has a substantially cylindrical shape. In one or more embodiments, the proximal portion 916 tapers in a distal direction. In one or more embodiments, the proximal portion 916 has a conical shape. The disclosure is not limited to the cylindrical shape shown in the exemplary embodiment. The proximal portion 916 further comprises a cavity in fluid communication with the lumen, the cavity being configured to receive a hub of a luer connector. In one or more embodiments, the cavity can be configured to facilitate a loose fit between the cavity and the hub of the luer connector, wherein the needle hub 910 is secured by an at least one thread 918 or set of tabs included on an outer surface of the proximal portion 916. The at least one thread 918 is sized and to have a thread pattern that will engage with a standard ISO-2 type of luer fitting. In further embodiments, the cavity can be configured in a Luer Slip fitting to facilitate an interference fit between the cavity and the hub of the luer connector. In one or more embodiments, the interference fit can be configured to be sufficiently strong enough to not require a threaded connection or the at least one thread 918 in removably securing the cavity to the luer connector. In one or more embodiments, the at least one thread 918 can include an inclined thread pattern. In one or more embodiments, the at least one thread 918 can include a helical-shaped thread pattern. Such connectors are generally and commonly used as catheter and other fluid-tight protective connectors in medical applications. Further alternate embodiments are non-removably or removably assembled with a threaded connection, press-fit connection, adhesive connection or a combination thereof.

Figure 21:
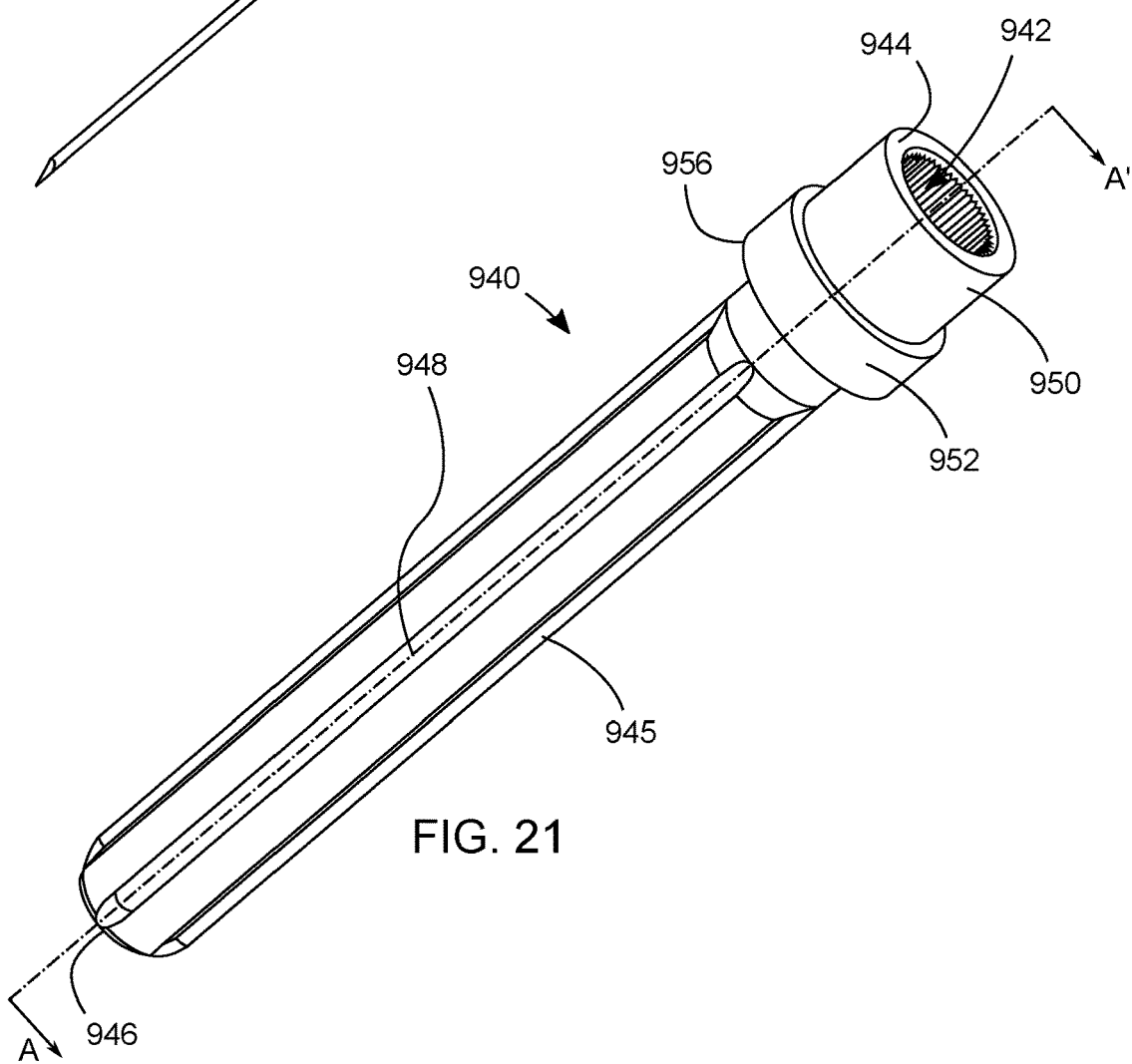
FIG. 21 illustrates a perspective view of a hard needle cover of the hard needle enclosure according to the second embodiment of the present disclosure.

As depicted in FIG. 21, the removable hard needle cover 940 comprises an elongated body having a cavity 942 defined by an open proximal end 944 and a closed distal end 946, the cavity 942 extending from the open proximal end 944 to the closed distal end 946. The elongated body further comprises a proximal portion 950, a medial portion 952 and a distal portion 945. The proximal portion 950 has a cylindrical surface configured to mate with the cap 970. The medial portion 952 is adjacent to the proximal portion 950 and is defined by a flange 956 extending from the elongated body of the removable hard needle cover 940. The distal portion 945 is adjacent to the medial portion 952, the distal portion comprising a plurality of grip members 948 extending from the closed distal end 946 along a surface of the elongated body.

Figure 22:
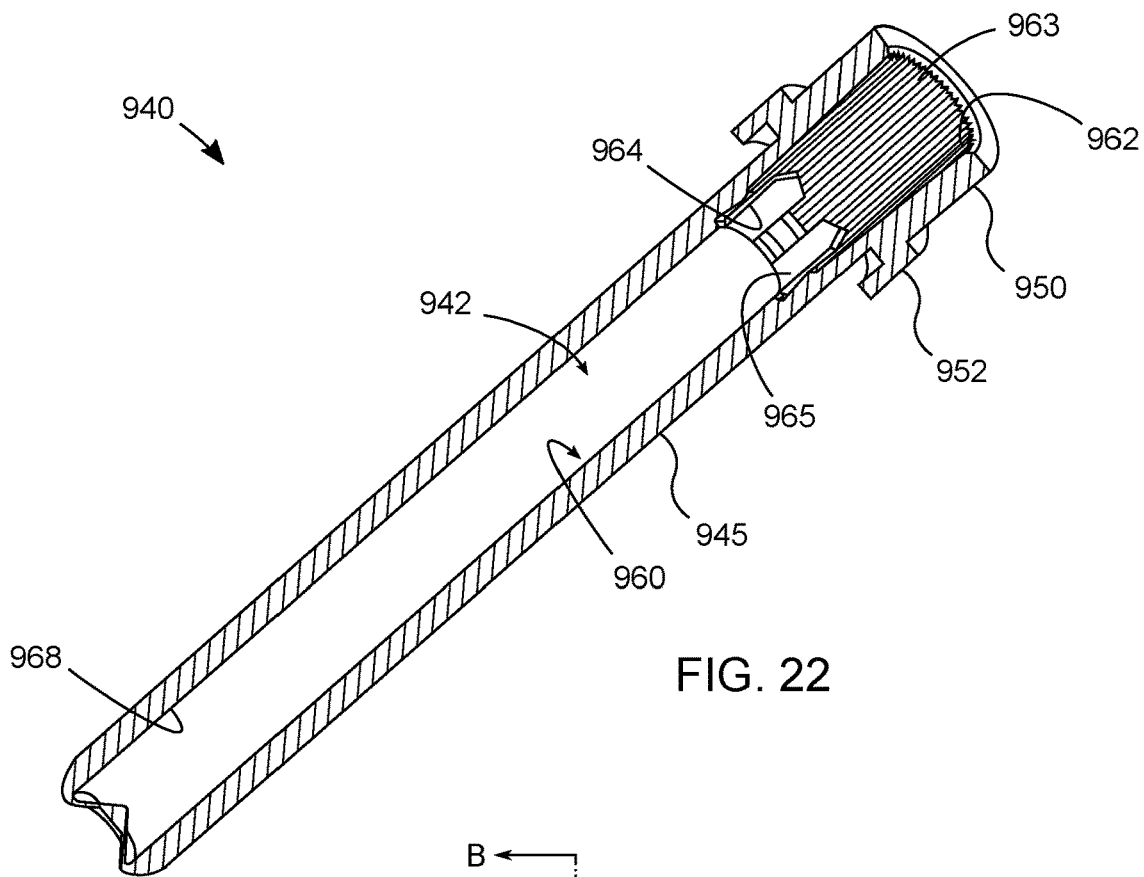
FIG. 22 illustrates a cross-sectional view of the hard needle cover of the hard needle enclosure according to the second embodiment of the present disclosure.

As shown in FIG. 22, an inner surface 960 of the cavity 942 comprises a proximal inner surface 962, a medial inner surface 964, and a distal inner surface 968. The proximal inner surface 962 includes a ribbed surface 963. The medial inner surface 964 includes a plurality of protrusions 965 extending from the medial surface 964. The plurality of protrusions 965 is configured to interdigitate with the plurality of longitudinal ribs 915 of the needle hub 910, the each of the plurality of longitudinal ribs 915 nesting between two of the plurality of protrusions 965, preventing rotational movement of the needle hub 910. The distal portion 945 is adjacent to the medial surface 964 and is configured to house the needle cannula 912 of the needle hub 910.

Figure 23:
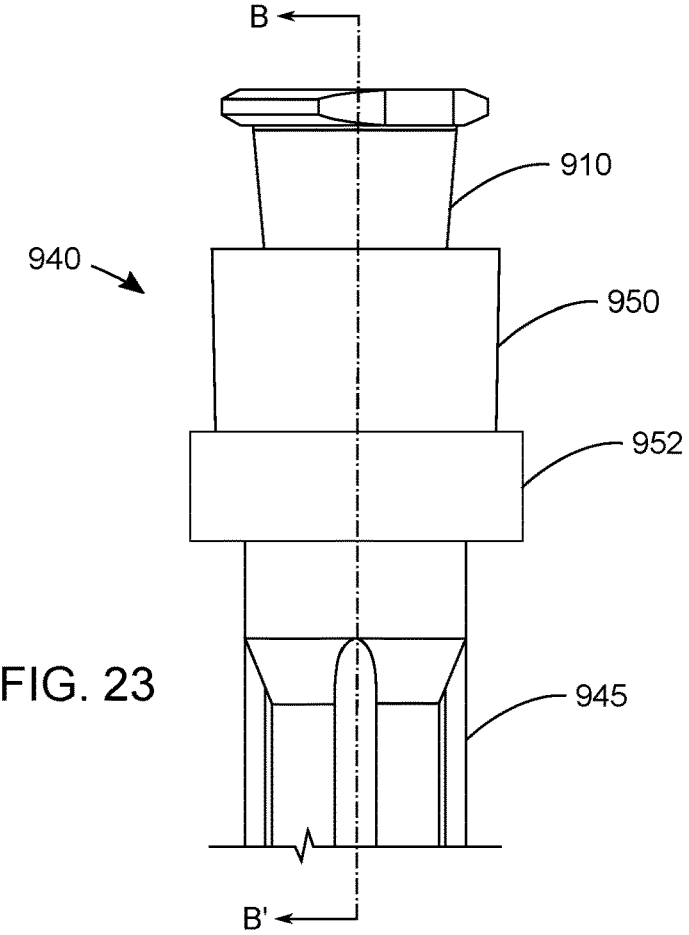
FIG. 23 illustrates a detailed side view of the hard needle enclosure according to the second embodiment of the present disclosure.
Figure 24:
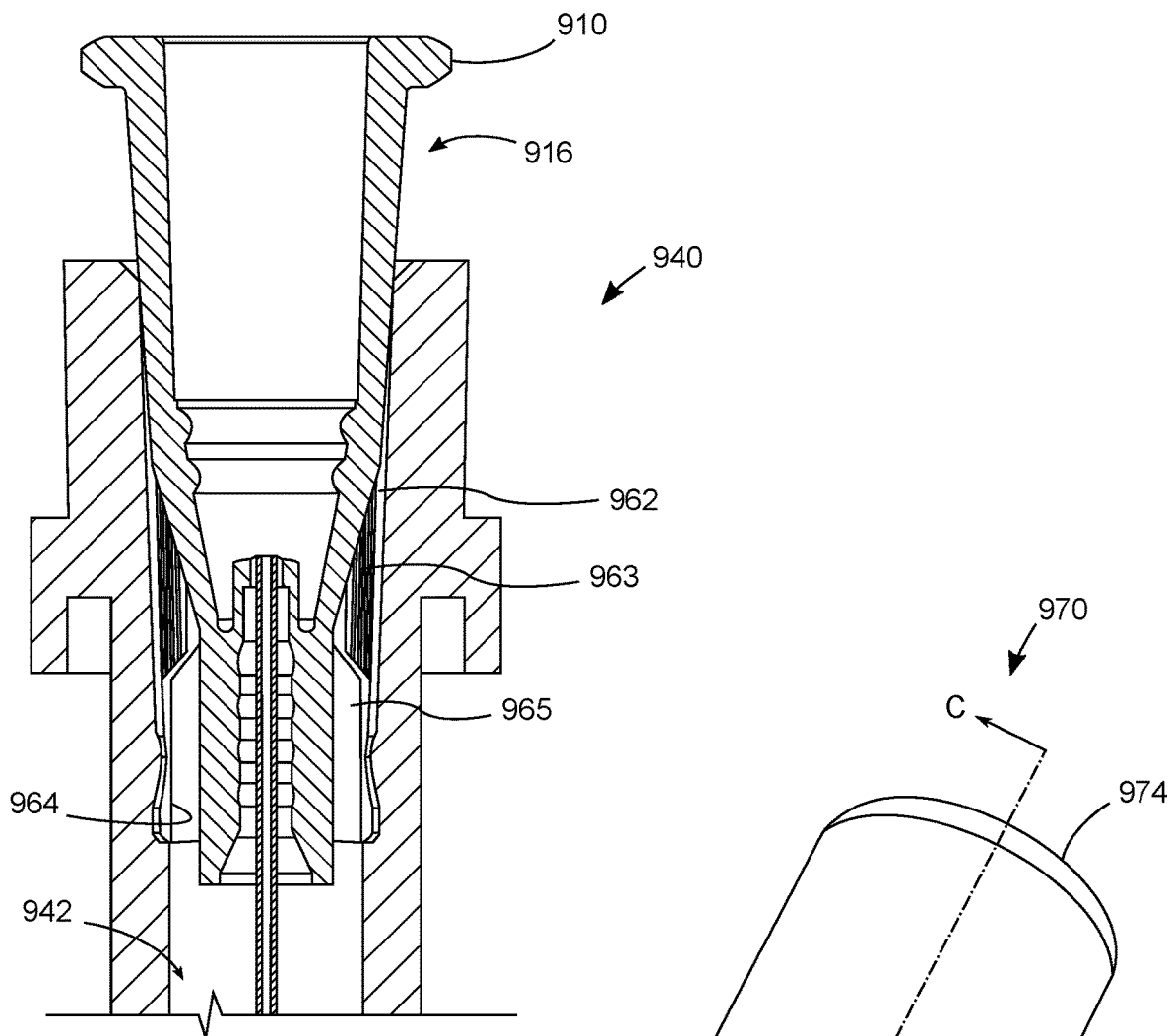
FIG. 24 illustrates a detailed cross-sectional view of the hard needle enclosure according to the second embodiment of the present disclosure.

As shown in FIGS. 23 and 24, the needle hub 910 is partially disposed within the removable hard needle cover 940. The proximal portion 916 of the needle hub 910 is partially disposed within the proximal inner surface 962 of the cavity 942 of the hard needle cover 940, creating a removable interference fit between the proximal portion 916 of the needle hub 910 and the ribbed surface 963 of the proximal inner surface 962. The plurality of protrusions 965 of the medial surface 964 interdigitate with the plurality of longitudinal ribs 915 of the distal portion 914 of the needle hub 910. In this configuration, the needle hub 910 cannot rotate due to the plurality of protrusions 965 of the medial surface 964 interdigitating with the plurality of longitudinal ribs 915, and the needle hub 910 cannot be unintentionally removed from the hard needle cover 940 due to the interference fit between the proximal portion 916 of the needle hub 910 and the ribbed surface 963 of the proximal inner surface 962. The ribbed surface 963 of the proximal inner surface 962 is further configured to allow air to flow around the needle hub 910 thereby preventing a vacuum due to changes in the atmosphere, which would otherwise require a greater force to remove beyond breaking the interference fit.

Figure 25:
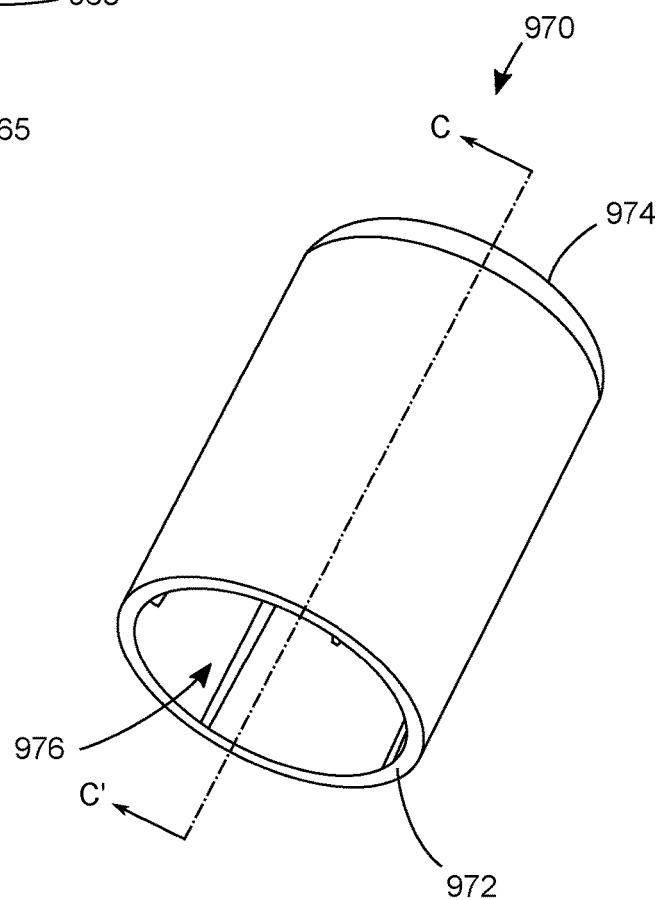
FIG. 25 illustrates a perspective view of a cap of the hard needle enclosure according to the second embodiment of the present disclosure.
Figure 26:
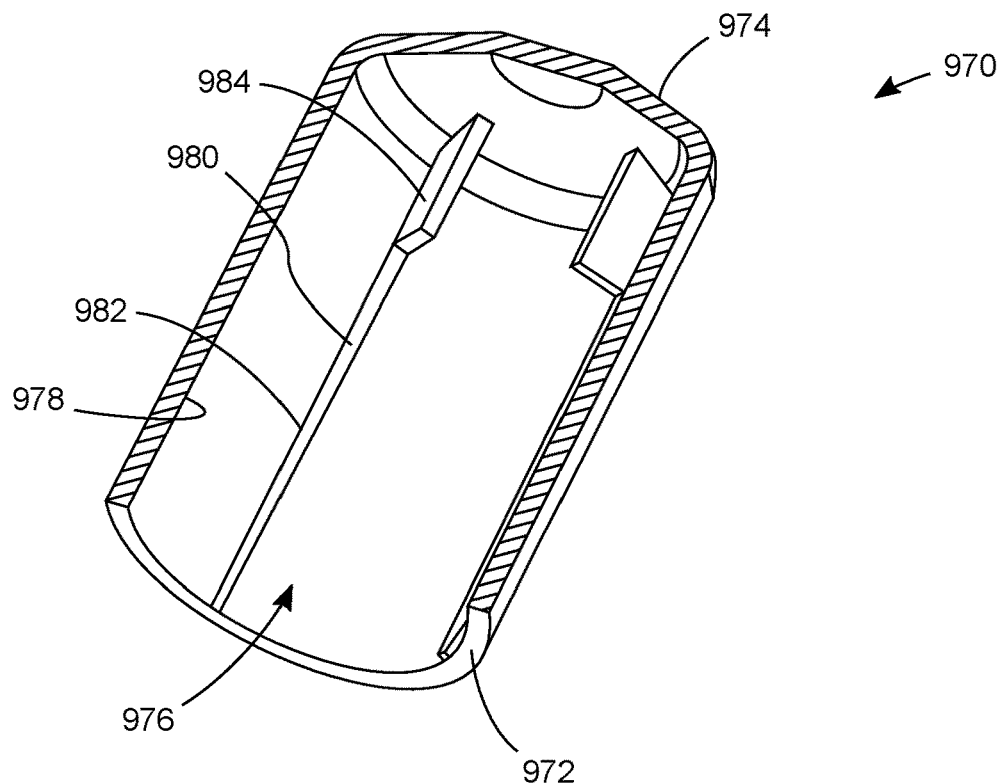
FIG. 26 illustrates a cross-sectional view perspective view of the cap of the hard needle enclosure according to the second embodiment of the present disclosure.

As shown in FIGS. 25 and 26, the cap 970 comprises a substantially cylindrical body having an open distal end 972 and a closed proximal end 974, the open distal end 972 and the closed proximal end 974 defining a cavity 976. From an inner surface 978 of the cavity extends a plurality of protrusions 980. The plurality of protrusions 980 extend longitudinally from the inner surface 978 and comprises a distal portion 982 which is adjacent to the open distal end 972 and a proximal portion 984 which is adjacent to the proximal end 974. The distal portion 982 of the plurality of protrusions 980 tapers inwardly from the open distal end 972 to the proximal portion 984, the taper configured to create an interference fit with the proximal portion 950 of the needle cover 940 upon insertion of the cap 970 over the proximal portion 950 of the needle cover 940. The proximal portion 984 of the plurality of protrusions 980 extends further from the inner surface 978 of the cap 970 and is configured to abut the proximal portion 916 of the needle hub 910 upon insertion of the cap 970 over the proximal portion 950 of the needle cover 940.

Figure 27:
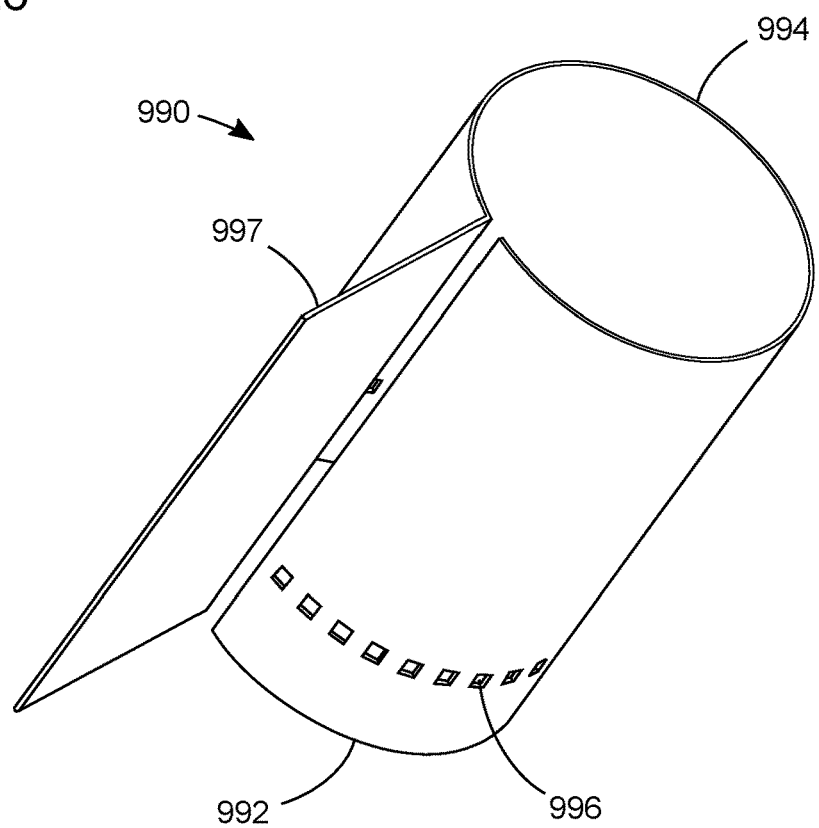
FIG. 27 illustrates a perspective view of a removable sleeve of the hard needle enclosure according to the second embodiment of the present disclosure.

As shown in FIG. 27, the sleeve 990 can be formed into a cylindrical shape comprising an open distal end 992 and an open proximal end 994. A plurality of perforations 996 are disposed radially around the cylindrical shape, the plurality of perforations 996 are configured to break upon separation of the needle cover 940 from the cap 970. In one or more embodiments, the sleeve 990 further includes a tab 997 integrally formed with the sleeve 990. In one or more embodiments, the tab 997 may include labeling or instructions. In one or more embodiments, the sleeve 990 is heat-sealed or induction sealed to the needle cover 940 and the cap 970. In one or more embodiments, the sleeve 990 is configured as a tamper-evident seal.

Figure 28:
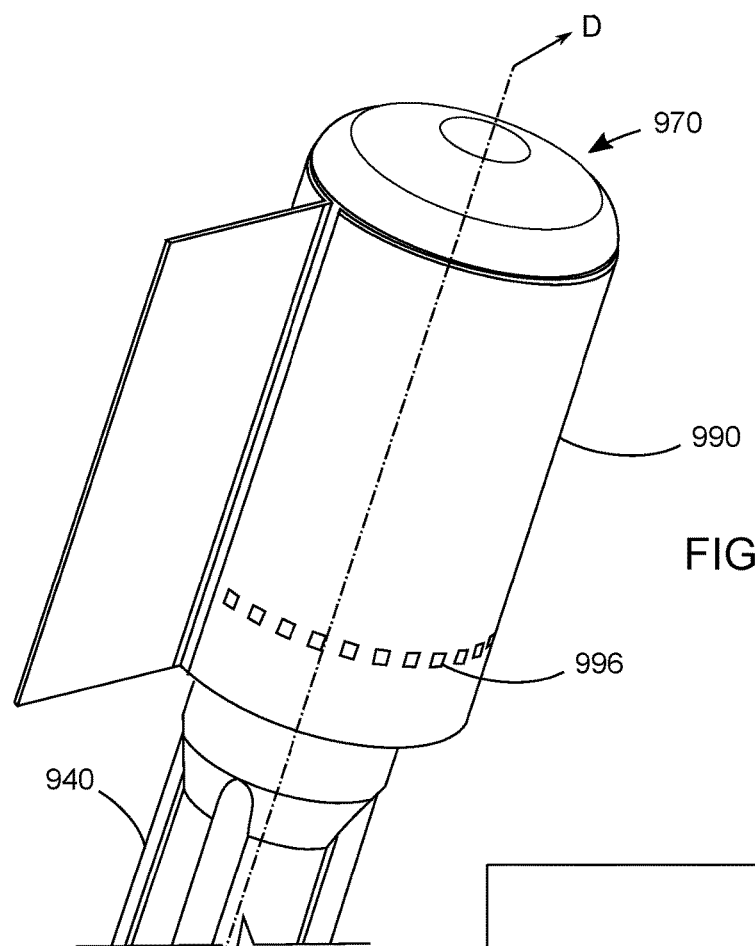
FIG. 28 illustrates a perspective side view of the hard needle enclosure according to the second embodiment of the present disclosure.
Figure 29:
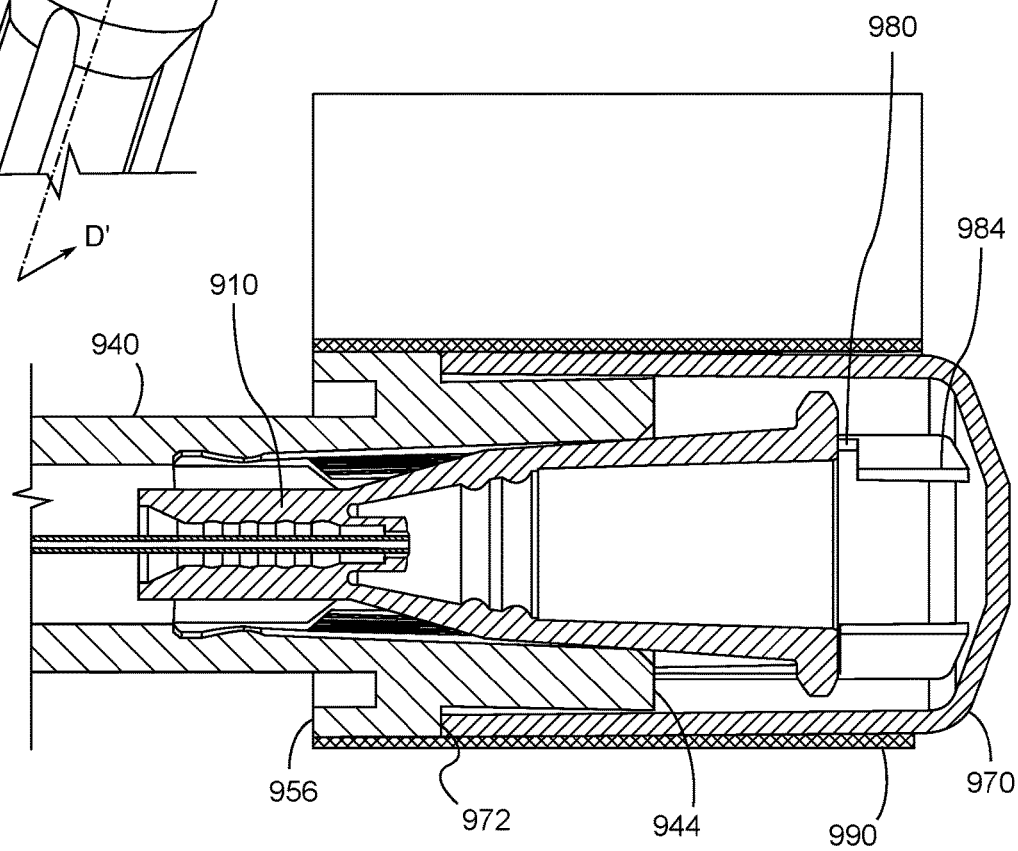
FIG. 29 illustrates a cross-sectional view of the hard needle enclosure according to the second embodiment of the present disclosure.

As shown in FIGS. 28 and 29, fully assembled, the sleeve 990 covers both the cap 970 and the proximal end 944 of the needle cover 940. The open distal end 972 of the cap 970 abuts the flange 956 of the needle cover 940. The open distal end 972 fully covers the open proximal end 944 of the needle cover 940. The plurality of perforations 996 are near or directly over the open distal end 972 of the cap 970 and the open proximal end 944 of the needle cover 940. As shown in FIG. 29, the proximal portion 984 of the plurality of protrusions 980 of the cap 970 limits the movement of the needle hub 910.

Figure 30:
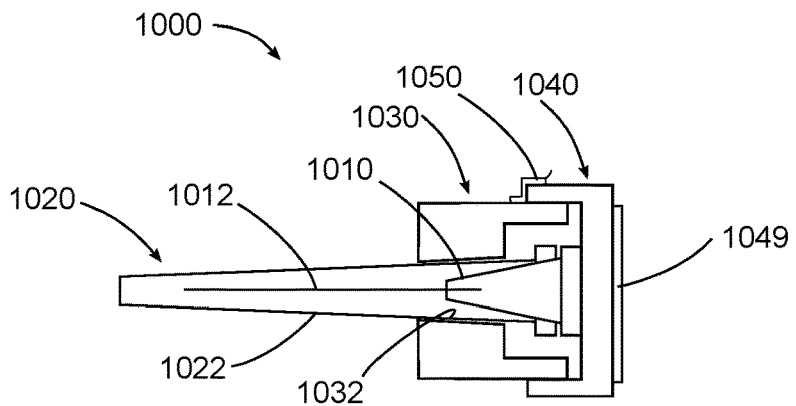
FIG. 30 illustrates a cross-sectional view of a hard needle enclosure according to a third embodiment of the present disclosure.
Figure 31:
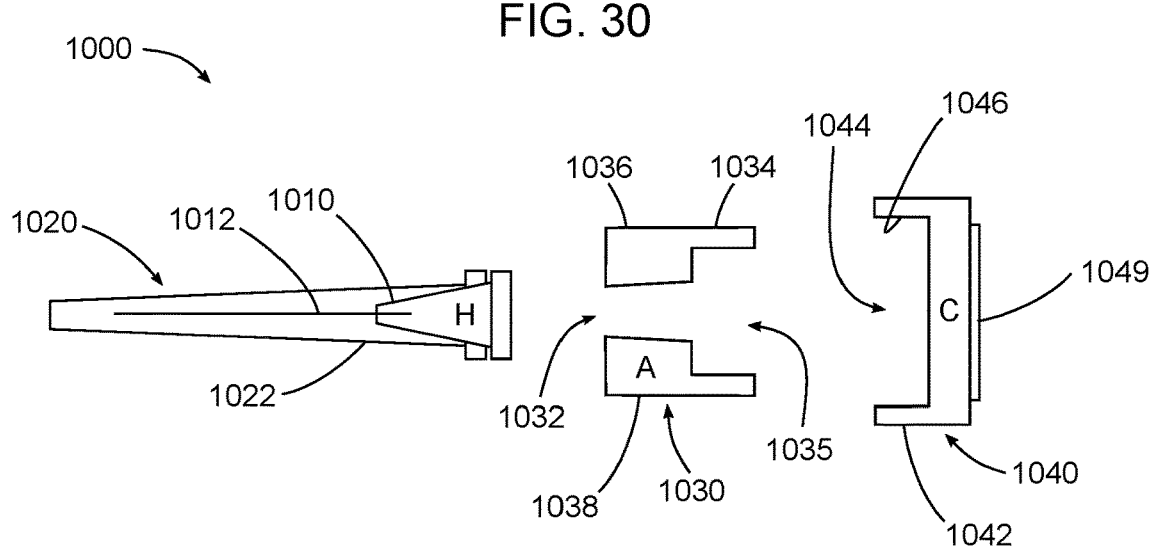
FIG. 31 illustrates a cross-sectional exploded view of the hard needle enclosure according to a third embodiment of the present disclosure.

As shown in FIGS. 30 and 31, a third embodiment of a safety needle device including hard needle enclosure 1000 comprises a needle hub 1010, a needle cover 1020, an adapter 1030 and a cap 1040, with FIG. 19 showing an assembled view and FIG. 20 showing an exploded view of the hard needle enclosure 1000. FIGS. 30 and 31 are cross-sectional views of substantially cylindrical bodies. The needle cover 1020 covers a needle cannula 1012, the needle cannula 1012 being disposed within a lumen of the needle hub 1010. The needle cover 1020 has a tapered cylindrical outer surface 1022 which when connected to the adapter creates or forms an interference fit and a sterility barrier with a tapered aperture 1032 of the adapter 1030.

The adapter 1030 comprises a substantially cylindrical body having a proximal portion 1034, a distal portion 1036 and an outside cylindrical surface 1038. The proximal portion 1034 has a proximal cavity 1035 in communication with the tapered aperture 1032 of the distal portion 1036. The tapered aperture 1032 is configured to create an interference fit with the tapered cylindrical surface 1022 of the needle cover 1020. The cap 1040 has a substantially cylindrical shape with a distal opening 1042 defining a distal cavity 1044. The cap 1040 is configured to interdigitate with the adapter 1030 by way of the distal cavity 1044 of the cap 1040 receiving the proximal portion 1034 of the adapter 1030. The outside cylindrical surface 1038 creates or forms an interference fit and a sterility barrier with an inside surface 1046 of the distal cavity 1044 when the two parts are connected. In one or more embodiments, the outside cylindrical surface 1038 creates or forms a snap fit and a sterility barrier with the inside surface 1046 of the distal cavity 1044 when the two parts are connected. Since a sterility barrier is provided by the fit between the outside cylindrical surface 1038 and the inside surface 1046, the need for a blister pack is eliminated, lowering the cost of packaging of needle devices compared to convention needle devices that require a blister pack to provide a sterility barrier. In one or more embodiments, the outside cylindrical surface 1038 is removably bonded with adhesive onto the inside surface 1046 of the distal cavity 1044. In one or more embodiments, the outside cylindrical surface 1038 is threaded into the inside surface 1046 of the distal cavity 1044. In one or more embodiments, the cap 1040 fits within the distal cavity 1044 of the adapter 1030. In one or more embodiments, a sticker label can be disposed on the cap to allow for marking pertaining to the contents of the hard needle enclosure 1000. In one or more embodiments, a label 1049 is placed on the cap 1040 distal end. In one or more embodiments, the label 1049 indicates that the hard needle enclosure 1000 has been opened or used. In one or more embodiments, the label 1049 includes words, numbers or symbols. In one or more embodiments, the label 1049 includes a biohazard symbol. In one or more embodiments, as shown in FIG. 30, a tamper-evident seal 1050 is incorporated where the cap 1040 and the adapter 1030 are joined to indicate when the cap 1040 and the adapter 1030 have been separated. In some embodiments, the tamper-evident seal 1050 is a sticker or a peel off label or tear away label. The disclosure is not limited to the cylindrical shape of exemplary embodiments shown.

The needle device including the hard needle enclosure 1000 is shipped and stored fully assembled. In operation, a practitioner first removes the cap 1040 from the adapter 1030 and then removes the needle hub 1010 and needle cover 1020 from the adapter 1030. In one or more embodiments, the tapered aperture 1032 of the adapter 1030 is configured to interdigitate with conventional needles or commercially available needles.

Figure 32:
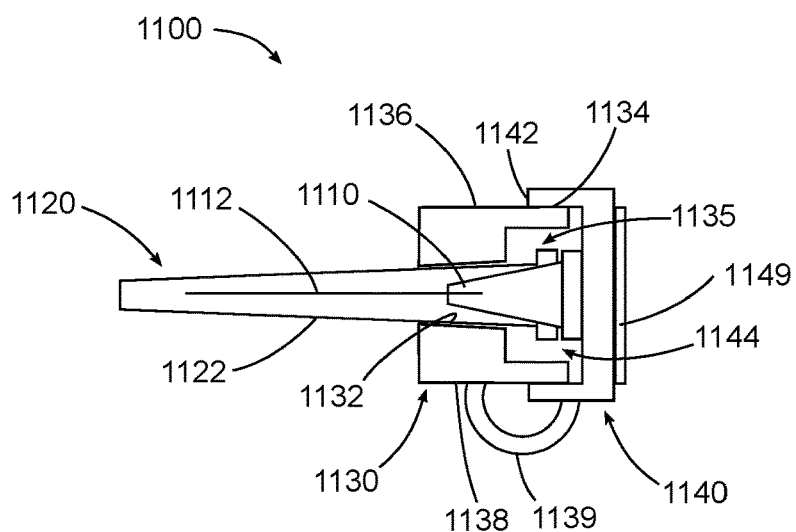
FIG. 32 illustrates a cross-sectional view of a hard needle enclosure according to a fourth embodiment of the present disclosure.

As shown in FIGS. 32 and 33, a fourth embodiment of a hard needle enclosure 1100 comprises a needle hub 1110, a needle cover 1120, an adapter 1130 and a cap 1140, with FIG. 21 showing an assembled view and FIG. 22 showing an exploded view of the hard needle enclosure 1100. FIGS. 32 and 33 are cross-sectional views of substantially cylindrical bodies. The needle cover 1120 covers a needle cannula 1112, the needle cannula 1112 being disposed within a lumen of the needle hub 1110. The needle cover 1120 has a tapered cylindrical surface 1122 which creates or forms an interference fit and a sterility barrier with a tapered aperture 1132 of the adapter 1130 when the two parts are connected.

The adapter 1130 comprises a substantially cylindrical body having a proximal portion 1134, a distal portion 1136 and a hinge 1139 disposed on an outside cylindrical surface 1138 of the adapter 1130. The proximal portion 1134 has a proximal cavity 1135 in communication with the tapered aperture 1132 of the distal portion 1136. The tapered aperture 1132 is configured to create an interference fit with the tapered cylindrical surface 1122 of the needle cover 1120.

The cap 1140 has a substantially cylindrical shape with a distal opening 1142 defining a distal cavity 1144. The cap 1140 is configured to interdigitate with the adapter 1130 by way of the distal cavity 1144 of the cap 1140 receiving the proximal portion 1134 of the adapter 1130. The hinge 1139 has a distal connection to the outside cylindrical surface 1138 of the adapter 1130 and a proximal connection to an outside cylindrical surface 1150 of the cap 1140.

The outside cylindrical surface 1138 creates or forms an interference fit and a sterility barrier with an inside surface 1146 of the distal cavity 1144 when the two parts are connected. In one or more embodiments, the outside cylindrical surface 1138 creates or forms a snap fit and a sterility barrier with the inside surface 1146 of the distal cavity 1144 when the two parts are connected. In one or more embodiments, the outside cylindrical surface 1138 is removably bonded with adhesive onto the inside surface 1146 of the distal cavity 1144. In one or more embodiments, the outside cylindrical surface 1138 is threaded into the inside surface 1146 of the distal cavity 1144. In one or more embodiments, the cap 1140 fits within the distal cavity 1144 of the adapter 1130. In one or more embodiments, a sticker label can be disposed on the cap to allow for marking pertaining to the contents of the hard needle enclosure 1100. In one or more embodiments, a label 1149 is placed on the cap 1140 distal end. In one or more embodiments, the label 1149 indicates that the hard needle enclosure 1100 has been opened or used. In one or more embodiments, the label 1149 includes words, numbers or symbols. In one or more embodiments, the label 1149 includes a biohazard symbol. In one or more embodiments, a tamper-evident seal (not shown) similar to the tamper evident seal 1050 shown in FIG. 30 is incorporated where the cap 1140 and the adapter 1130 are joined to indicate when the cap 1140 and the adapter 1130 have been separated. In some embodiments, the tamper-evident seal is a sticker or a peel off label or tear away label. The disclosure is not limited to the cylindrical shape of exemplary embodiments shown.

Figure 33A:
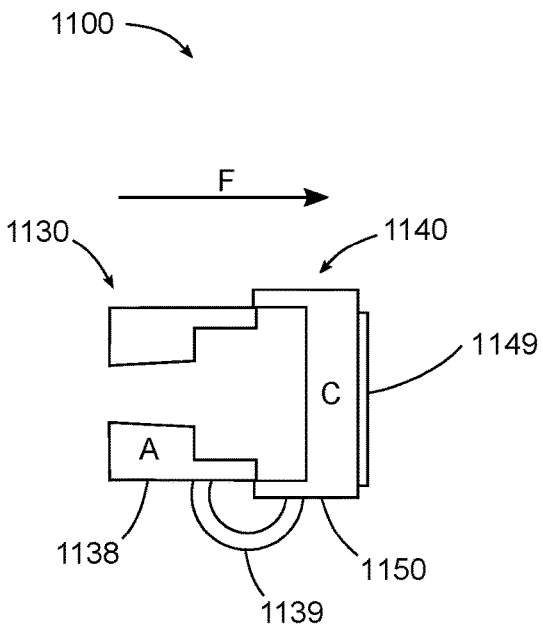
FIG. 33A illustrates a cross-sectional view of an adapter of the hard needle enclosure according to the fourth embodiment of the present disclosure.
Figure 33B:
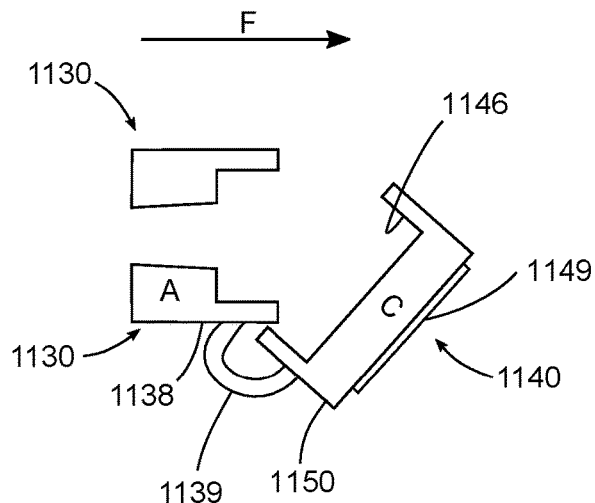
FIG. 33B illustrates the adapter of the hard needle disclosure shown in FIG. 33A upon application of force F.

The needle device including the hard needle enclosure 1100 is shipped and stored fully assembled. In operation, a practitioner first removes the cap 1140 from the adapter 1130 and then removes the needle hub 1110 and needle cover 1120 from the adapter 1130. Referring to FIGS. 33A and 33B, the hard needle enclosure is opened with one handed operation by applying a proximal force F against the outside cylindrical surface 1138 of the adapter 1130 opposite the hinge 1139, as shown in FIG. 33B. In one or more embodiments, the tapered aperture 1132 of the adapter 1130 is configured to interdigitate with conventional needles or commercially available needles. The disclosure is not limited to the cylindrical shape of exemplary embodiments shown.

Figure 34:
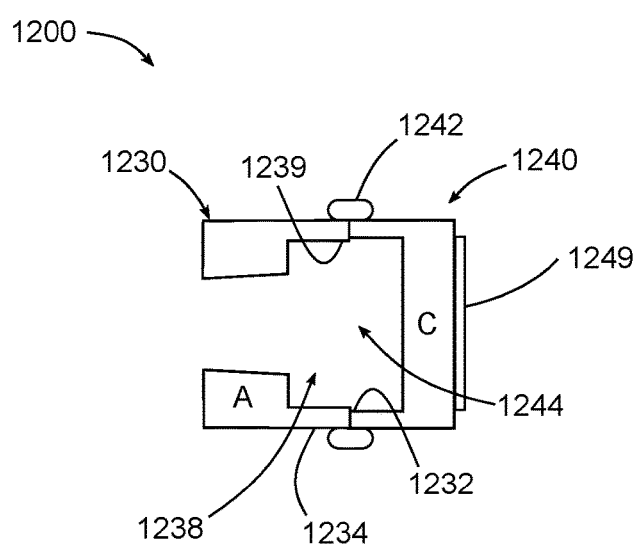
FIG. 34 illustrates a cross-sectional view of a hard needle enclosure according to a fifth embodiment of the present disclosure.

As shown in FIG. 34, a fifth embodiment of a hard needle enclosure 1200 comprises a needle hub, a needle cover, an adapter 1230 and a cap 1240. FIG. 34 is a cross-sectional view of substantially cylindrical bodies. The needle cover covers a needle cannula, the needle cannula being disposed within a lumen of the needle hub. The needle cover has a tapered cylindrical surface which creates or forms an interference fit and a sterility barrier with a tapered aperture of the adapter 1230 when the two parts are connected.

The adapter 1230 comprises a substantially cylindrical body having a proximal portion 1234 having a cavity 1238 defined by a proximal opening 1239 and a distal portion 1236. The cap 1240 has a substantially cylindrical shape with a distal opening 1232 defining a distal cavity 1244. Fully assembled, the proximal opening 1239 and the distal opening 1232 abut each other. The proximal opening 1239 and the distal opening 1232 are removably bonded together with adhesive 1242. In one or more embodiments, a label 1249 is placed on the cap 1240 distal end. In one or more embodiments, the label 1249 indicates that the hard needle enclosure 1200 has been opened or used. In one or more embodiments, the label 1249 includes words, numbers or symbols. In one or more embodiments, the label 1249 includes a biohazard symbol. In one or more embodiments, a tamper-evident seal (not shown) similar to the tamper evident seal 1050 shown in FIG. 30 is incorporated where the cap 1240 and the adapter 1230 are joined to indicate when the cap 1240 and the adapter 1230 have been separated. In some embodiments, the tamper-evident seal is a sticker or a peel off label or tear away label. The disclosure is not limited to the cylindrical shape of exemplary embodiments shown.

As shown in FIG. 35, a sixth embodiment of a hard needle enclosure 1300 comprises a needle hub 1310, a needle cover 1320, an adapter 1330 and a cap 1340, with FIG. 24 showing an exploded view of the hard needle enclosure 1300. FIG. 35 is a cross-sectional view of substantially cylindrical bodies. The needle cover 1320 covers a needle cannula 1312, the needle cannula 1312 being disposed within a lumen of the needle hub 1310. The needle cover 1320 has a tapered cylindrical surface 1322 which creates or forms an interference fit and a sterility barrier with a tapered aperture 1332 of the adapter 1330 when the two parts are connected.

The adapter 1330 comprises a substantially cylindrical body having a proximal portion 1334, a distal portion 1336 and an outside surface 1338. The proximal portion 1334 has a proximal cavity 1335 in communication with the tapered aperture 1332 of the distal portion 1336. The tapered aperture 1332 is configured to create an interference fit with the tapered cylindrical surface 1322 of the needle cover 1320. The cap 1340 has a substantially cylindrical shape with a distal opening 1342 defining a first cavity 1344. In one or more embodiments, the first cavity 1344 forms a distal wall 1365 on which a label 1349 is placed. In one or more embodiments, the label 1349 indicates that the hard needle enclosure 1300 has been opened or used. In one or more embodiments, the label 1349 includes words, numbers or symbols. In one or more embodiments, the label 1349 includes a biohazard symbol.

The cap 1340 is configured to interdigitate with the adapter 1330 by way of the first cavity 1344 of the cap 1340 receiving the proximal portion 1334 of the adapter 1330. The outside surface 1338 creates or forms an interference fit and a sterility barrier with an inside surface 1346 of the first cavity 1344 when the two parts are connected. In one or more embodiments, the outside surface 1338 creates or forms a snap fit and a sterility barrier with the inside surface 1346 of the first cavity 1344 when the two parts are connected. In one or more embodiments, the outside surface 1338 is removably bonded with adhesive onto the inside surface 1346 of the first cavity 1344. In one or more embodiments, the outside surface 1338 is threaded into the inside surface 1346 of the first cavity 1344. In one or more embodiments, the cap 1340 fits within the first cavity 1344 of the adapter 1330. In one or more embodiments, a sticker label can be disposed on the cap to allow for marking pertaining to the contents of the hard needle enclosure 1300. In one or more embodiments, a label 1349 is placed on the cap 1340 distal end. In one or more embodiments, the label 1349 indicates that the hard needle enclosure 1300 has been opened or used. In one or more embodiments, the label 1349 includes words, numbers or symbols. In one or more embodiments, the label 1349 includes a biohazard symbol.

In one or more embodiments, a tamper-evident seal (not shown) similar to the tamper evident seal 1050 shown in FIG. 30 is incorporated where the cap 1340 and the adapter 1330 are joined to indicate when the cap 1340 and the adapter 1330 have been separated. In some embodiments, the tamper-evident seal is a sticker or a peel off label or tear away label.

The cap further comprises a second cavity 1350 having an inside surface 1352. The second cavity 1350 is configured to interdigitate with the adapter 1330. The outside surface 1338 of the adapter 1330 creates or forms an interference fit and a sterility barrier with an inside surface 1352 of the first cavity 1344 when the two parts are connected. The disclosure is not limited to the cylindrical shape of exemplary embodiments shown.

As shown in FIGS. 36-37, in one or more embodiments, the adapter 1330 and the cap 1340 each comprise tabs which are either configured to removably or non-removably snap into each other. More specifically, the adapter 1330 includes an adapter tab or an adapter ledge 1339 having a locking surface 1339a and a ramped surface 1339b. In the embodiment shown, the adapter tab or the adapter ledge 1339 has a triangular shape, wherein the locking surface 1339a on a right angle face of the adapter tab or the adapter ledge 1339, which is located opposite to the ramped surface 1339b of the adapter tab or the adapter ledge 1339. As shown in FIGS. 36 and 37, the right angle face is substantially perpendicular to the outside surface 1338 of the adapter 1330. The adapter tab or the adapter ledge 1339 can be a singular continuous feature located on a proximal end of the adapter 1330, or there could be a plurality (e.g. two, three, four or more) of discrete adapter tabs or adapter ledges 1339 disposed and spaced apart on the outside surface 1338 of the adapter 1330.

The cap 1340 comprises a holding tab or a bump 1354 disposed on the inside surface 1346 of the first cavity 1344. The holding tab or the bump 1354 is configured to removably or releasably snap-fit with the adapter tab or the adapter ledge 1339 of the adapter 1330 upon insertion of the adapter 1330 into the first cavity 1344 of the cap 1340. The holding tab or the bump comprises a first ramped surface 1354a and a second ramped surface 1354b, which slidably engage the locking surface 1339a and the ramped surface 1339b of the adapter tab or adapter ledge 1339. The holding tab or the bump 1354 can be a singular continuous feature, or there could be a plurality (e.g. two, three, four or more) of discrete holding tabs or bumps disposed and spaced apart on the inside surface 1346 of the first cavity 1344. The first cavity 1344 is facing in a distal direction when the hard needle enclosure packages a new needle cannula 1312.

The cap 1340 further comprises a locking tab or a cap ledge 1358 disposed on the inside surface 1352 of the second cavity 1350. The locking tab or cap ledge 1358 of the second cavity 1350 has a triangular shape, wherein there is a locking surface 1358a on a right angle face of the locking tab or the cap ledge 1358, which is located opposite a sloped surface 1358b of the locking tab or the cap ledge 1358 when the cap 1340 is mounted to a newly packaged needle cannula 1312. As shown in FIGS. 36 and 37, the right angle face is substantially perpendicular to the inside surface 1352 of the second cavity 1350. The locking surface 1358a of the first cavity 1344 is configured to create a non-removable or irreversible snap fit with the locking surface 1339a of adapter tab or adapter ledge 1339 of the adapter 1330 upon insertion of the adapter 1330 into the second cavity 1350 of the cap 1340. The locking tab or the cap ledge 1358 can be a singular continuous feature, or there could be a plurality (e.g. two, three, four or more) of discrete locking tabs or cap ledges disposed and spaced apart on the inside surface 1352 of the second cavity 1350. In FIG. 37, when the cap 1340 is in the locked position, the second cavity 1350 is facing in the distal direction and the first cavity 1344 is facing in the proximal direction.

The embodiment shown and described with respect to FIGS. 36 and 37 is exemplary only. According to an embodiment of the disclosure, the adapter comprises an adapter locking feature, exemplified as the adapter tab or the adapter ledge 1339, that interacts with a reversible or releasable holding feature, exemplified as the holding tab or bump 1354 in the first cavity 1344 a locking tab or a cap ledge 1358 in the second cavity 1354 of the cap 1340. However, according to one or more embodiments, the adapter can include an adapter holding and lock feature different from that shown in FIGS. 36 and 37 that interacts with a cap holding feature in the first cavity 1344 to provide a releasable or reversible attachment of the cap 1340 to the adapter 1330 and a cap locking feature in the second cavity 1350 of the cap 1340. Thus, in one or more embodiments, the adapter and the first cavity are configured to be releasably connected and the adapter and the second cavity are configured to be connected in a locked configuration where they cap and the adapter cannot be released once they are locked.

According to one or more embodiments, the first cavity 1344 comprises first indicia 1349a inside and visible and/or tactilely discernable by a person, the first indicia 1349a denoting that the hard-packaged safety needle device including the needle cannula 1312 has been used and that the device should be discarded. This first indicia 1349a in some embodiments comprises a symbol, such as a biohazard symbol, words such as "used" or "do not use," or other suitable visual or tactile indicia denoting a used device that should be discarded and not reused. It will be appreciated that when the cap 1340 is in the configuration shown in FIG. 36, when the first indicia denoting that the hard-packaged safety needle device including the needle cannula 1312 has not been used, the first indica 1349a is not visible or tactilely discernable. The second cavity 1350 of the cap 1340 may further comprise second indicia 1349b indicating that the hard-packaged safety needle device is ready for use. The second indicia 1349 in some embodiments comprises a symbol or words such as "ready for use" or information about the device such as needle gauge and length. The symbol in some embodiments may include a corporate logo.

After the hard-packaged safety needle device has been used and the cap 1340 is reversed from the configuration shown in FIG. 36, and slidably inserted onto the adapter 1330 so that the cap 1340 locks onto the adapter as shown in FIG. 37, where the cap 1340 is in a position to be slidably engaged with the adapter 1330. In this position, the first indicia 1349a is now visible and/or tactilely discernable by a person. When the person sees the first indicia 1349a or touches the first indicia 1349a, they will be informed that the device has been used, and that the device should not be reused and discarded.

While the present disclosure has been shown and described with reference to certain exemplary embodiments thereof, it will be understood by those skilled in the art that various changes in form and details may be made therein without departing from the spirit and scope of the embodiments of the present disclosure. Also, the inner and/or the outer housing of the disinfection cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A safety needle device comprising:
a needle hub configured to couple to a syringe, the needle hub comprising a distal portion and a proximal portion, the needle hub having a substantially cylindrical shape;
a needle cannula extending from the distal portion of the needle hub;
a removable collar having a substantially cylindrical body, an aperture extending through the substantially cylindrical body, and two attachment points disposed on an outer surface of the collar, the aperture being sized and configured to receive the proximal portion of the needle hub; the two attachment points being configured to attach to a two-piece hinged cap; and,
a two-piece hinged cap having two elongated bodies in a clamshell configuration, the two elongated bodies configured to close in on one another, each of the two elongated bodies having a push feature with a right face and a hypotenuse face, the right face having an aperture and the hypotenuse face having a textured surface, each of the two elongated bodies having a semicircular cross-section and a cavity defined by an open proximal end and a closed distal end, loops extend from the open proximal end, the loops configured to interdigitate with the two attachment points of the collar.

2. The safety needle device of claim 1, wherein the proximal portion of the needle hub tapers in a distal direction.

3. The safety needle device of claim 1, wherein the aperture of the collar is sized and configured to create an interference fit with the proximal portion of the needle hub.

4. The safety needle device of claim 1, wherein the aperture of the collar is sized and configured to create a loose fit with the proximal portion of the needle hub.

5. The safety needle device of claim 1, wherein the collar freely rotates around the proximal portion of the needle hub.

6. The safety needle device of claim 1, wherein the collar is configured to snap into the needle hub creating an interference fit, the collar being configured to freely rotate only upon application of sufficient force, thereby resisting free movement.

7. The safety needle device of claim 1, wherein the two attachment points are configured as hooks sized to receive the loops of the two-piece hinged cap and the two attachment points are sized and shaped to create a snap fit or an interference fit with the loops of the two-piece hinged cap.

8. The safety needle device of claim 1, wherein the two attachment points are configured as a living hinge configured to have a residual spring action, wherein the living hinge is in an open state in its resting position and the open state of the living hinge resists movement of the two-piece hinged cap.

9. The safety needle device of claim 1, wherein the elongated bodies of the two-piece hinged cap are configured to snap together upon full closure.

10. The safety needle device of claim 1, wherein two-piece hinged cap is configured to freely move and the collar is configured to freely rotate around the needle hub in an open state of the safety needle device.

11. The safety needle device of claim 10, wherein each of the two-piece hinged cap is freely able to open or close independently.

12. The safety needle device of claim 10, wherein the two-piece hinged cap is movable from 0 degrees with respect to the cannula to at least 125 degrees with respect to the needle cannula.

13. The safety needle device of claim 1, wherein the two-piece hinged cap is held closed by a disposable plastic seal or sleeve disposed over the two-piece hinged cap.

14. The safety needle device of claim 1, further comprising a sleeve disposed over the two-piece hinged cap in a closed state, the sleeve movable in a longitudinal direction over the two-piece hinged cap.

15. The safety needle device of claim 1, wherein a closed distal end of the two-piece hinged cap is configured to non-removably lock upon closure of the two-piece hinged cap, the closed distal end defining a final closed state.

16. The safety needle device of claim 15, the two-piece hinged cap further comprises a locking element disposed a distance from the closed distal end of the two-piece hinged cap.

17. The safety needle device of claim 16, the locking element comprising a hook tab projecting from an edge of one of the two-piece hinged cap and a corresponding aperture disposed within the cavity of the other of the two-piece hinged cap.

18. The safety needle device of claim 17, wherein the aperture is configured to interdigitate and removably or non-removably receive the hook tab.

19. The safety needle device of claim 18, wherein the aperture is configured to interdigitate and removably receive the hook tab in a closed state.

20. The safety needle device of claim 18, wherein the aperture is configured to interdigitate and non-removably receive the hook tab in a closed state.

21. The safety needle device of claim 1, the push features having a triangular shape, the hypotenuse face configured to abut a barrel surface of a syringe when the needle hub is connected to a Luer connector of the syringe.

22. The safety needle device of claim 21, the hypotenuse face configured to aid in pushing the two-piece hinged cap together.

23. The safety needle device of claim 22, wherein a right face of the triangular shape is configured to aid in pulling the two-piece hinged cap apart.

24. The safety needle device of claim 22, wherein the aperture of the right face of the push feature forms an edge between the aperture and the hypotenuse face, the hypotenuse face configured to aid in pulling the two-piece hinged cap apart.

* * * * *